US011837327B2

(12) United States Patent
Westcott et al.

(10) Patent No.: US 11,837,327 B2
(45) Date of Patent: Dec. 5, 2023

(54) SYSTEM AND METHOD FOR PROTEIN SELECTION

(71) Applicant: Climax Foods Inc., Berkeley, CA (US)

(72) Inventors: Daniel Westcott, Berkeley, CA (US); Jeffrey Johnson, Berkeley, CA (US); Di Wei, Berkeley, CA (US)

(73) Assignee: Climax Foods Inc., Berkeley, CA (US)

( * ) Notice: Subject to any disclaimer, the term of this patent is extended or adjusted under 35 U.S.C. 154(b) by 0 days.

(21) Appl. No.: 18/095,339

(22) Filed: Jan. 10, 2023

(65) Prior Publication Data

US 2023/0223109 A1 Jul. 13, 2023

Related U.S. Application Data

(60) Provisional application No. 63/298,920, filed on Jan. 12, 2022, provisional application No. 63/298,930, filed on Jan. 12, 2022, provisional application No. 63/298,927, filed on Jan. 12, 2022, provisional application No. 63/297,966, filed on Jan. 10, 2022.

(51) Int. Cl.
| | |
|---|---|
| *G01N 33/48* | (2006.01) |
| *G16B 30/00* | (2019.01) |
| *G16B 20/00* | (2019.01) |
| *G16B 15/20* | (2019.01) |
| *G16B 40/00* | (2019.01) |
| *G06N 3/08* | (2023.01) |
| *A23C 11/10* | (2021.01) |
| *A23C 20/02* | (2021.01) |
| *A23J 3/14* | (2006.01) |
| *A23J 3/22* | (2006.01) |
| *A23L 33/125* | (2016.01) |
| *A23L 33/135* | (2016.01) |
| *A23L 33/185* | (2016.01) |
| *G16B 15/00* | (2019.01) |
| *G16B 40/20* | (2019.01) |

(52) U.S. Cl.
CPC ............. *G16B 30/00* (2019.02); *A23C 11/10* (2013.01); *A23C 20/02* (2013.01); *A23J 3/14* (2013.01); *A23J 3/225* (2013.01); *A23J 3/227* (2013.01); *A23L 33/125* (2016.08); *A23L 33/135* (2016.08); *A23L 33/185* (2016.08); *G06N 3/08* (2013.01); *G16B 15/00* (2019.02); *G16B 15/20* (2019.02); *G16B 20/00* (2019.02); *G16B 40/00* (2019.02); *G16B 40/20* (2019.02)

(58) Field of Classification Search
None
See application file for complete search history.

(56) References Cited

U.S. PATENT DOCUMENTS

| | | | |
|---|---|---|---|
| 9,011,949 | B2 | 4/2015 | Brown et al. |
| 10,957,424 | B1 | 3/2021 | Navon et al. |
| 10,962,473 | B1 | 3/2021 | O'Hara et al. |
| 11,164,478 | B2 | 11/2021 | Pichara et al. |
| 11,205,101 | B1 | 12/2021 | Kawas Garcia et al. |
| 11,348,664 | B1 | 5/2022 | Kaneko et al. |
| 11,373,107 | B1 | 6/2022 | Clavero et al. |
| 11,404,144 | B1 | 8/2022 | Kang et al. |
| 2006/0205003 | A1 | 9/2006 | Gustafsson et al. |
| 2011/0059501 | A1 | 3/2011 | Davis |
| 2017/0091637 | A1 | 3/2017 | Chae et al. |
| 2017/0330097 | A1* | 11/2017 | Chae ..................... G06N 20/20 |
| 2021/0043272 | A1 | 2/2021 | Amimeur et al. |
| 2021/0174909 | A1 | 6/2021 | Rothberg et al. |
| 2022/0104515 | A1 | 4/2022 | Hume et al. |

OTHER PUBLICATIONS

Dietterich, Thomas G., Richard H. Lathrop, and Tomás Lozano-Pérez. "Solving the multiple instance problem with axis-parallel rectangles." Artificial intelligence 89.1-2 (1997): 31-71.*
"Are you on a mission to develop the next best plant-based food products?", Meat Alternative Company | Shiru—Approach.
"Ingredient biotech startup Shiru awarded key patent for protein discovery platform", Shiru, Sep. 13, 2022.
Day, Adrienne , "How one man's philosophy of data and food science could help save the planet", Grist.org, Nov. 10, 2020.
Ferreira, Alexander De Moura , "Machine Learning Prediction of Protein Abundance by Codon Usage Metrics", 2020, https://www.locus.ufv.br/bitstream/123456789/27942/1/texto%20completo.pdf.
Ferreira, Mauricio , et al., "Protein Abundance Prediction Through Machine Learning Methods", bioRxiv preprint doi: https://doi.org/10.1101/2020.09.17.302182; this version posted Sep. 19, 2020.
Ferreira, Mauricio , et al., "Protein Abundance Prediction Through Machine Learning Methods", Journal of Molecular Biology 433 (2021) 167267.
Shiebar, Jonathan , "Founded by an Impossible Foods and Google data scientist, Climax Foods raises $7.5 million to tackle the cheesiest market", Techcrunch, Sep. 1, 2020.
Watson, Elaine , "Climax Foods raises $7.5m: 'We want to replace animals as inefficient factories for converting blants into meat and dairy'", FoodNavigator-USA.com, Sep. 2, 2020.
Spanig, Sebastian , et al., "Encodings and models for antimicrobial peptide classification for multi-resistant pathogens", BioData Mining, 12, Article No. 7 (2019), https://biodatamining.biomedcentral.com/articles/10.1186/s13040-019-0196-x.

* cited by examiner

*Primary Examiner* — Anna Skibinsky
(74) *Attorney, Agent, or Firm* — Jeffrey Schox; Diana Lin

(57) ABSTRACT

The method for protein selection can include: characterizing a protein set, training a prediction model, determining target characteristic values, and determining a candidate protein set based on the target characteristic values.

18 Claims, 14 Drawing Sheets

| database | | | | | | | | |
|---|---|---|---|---|---|---|---|---|
| *source component* | *protein set* | *protein* | *protein%* | *process parameters* | *protein modification* | *AA sequence* | *feature values* | *functional property value set* |
| source component 1 | protein set 1 | protein 1 | 50% | process parameters A | mod 1 | AA sequence 1 | {features 1} | functional property values A |
| | | protein 2 | 50% | | mod 1 | AA sequence 2 | {features 2} | |
| source component 1 | protein set 1 | protein 1 | 50% | process parameters B | none | AA sequence 1 | {features 1} | functional property values B |
| | | protein 2 | 50% | | none | AA sequence 2 | {features 2} | |
| source component 2 | protein set 2 | protein 1 | 40% | process parameters C | none | AA sequence 1 | {features 1} | functional property values C |
| | | protein 3 | 30% | | none | AA sequence 3 | {features 3} | |
| | | protein 4 | 25% | | none | AA sequence 4 | {features 4} | |
| | | other | 5% | | none | | | |
| 50:50 mixture of source component 1 & 2 | protein set 3 | protein 1 | 45% | process parameters D | 50:50 mod1:none | AA sequence 1 | {features 1} | functional property values D |
| | | protein 2 | 25% | | mod 1 | AA sequence 2 | {features 2} | |
| | | protein 3 | 15% | | none | AA sequence 3 | {features 3} | |
| | | protein 4 | 12.5% | | none | AA sequence 4 | {features 4} | |
| | | other | 2.5% | | none | | | |

FIGURE 3

SYSTEM AND METHOD FOR PROTEIN SELECTION

CROSS-REFERENCE TO RELATED APPLICATIONS

This application claims the benefit of U.S. Provisional Application No. 63/297,966 filed 10 Jan. 2022, U.S. Provisional Application No. 63/298,920 filed 12 Jan. 2022, U.S. Provisional Application No. 63/298,927 filed 12 Jan. 2022, and U.S. Provisional Application No. 63/298,930 filed 12 Jan. 2022, each of which is incorporated in its entirety by this reference.

TECHNICAL FIELD

This invention relates generally to the food science field, and more specifically to a new and useful system and method in the food science field.

BRIEF DESCRIPTION OF THE FIGURES

FIG. 3 depicts an illustrative example of a database.

DETAILED DESCRIPTION

The following description of the embodiments of the invention is not intended to limit the invention to these embodiments, but rather to enable any person skilled in the art to make and use this invention.

1. OVERVIEW

Figure 1:
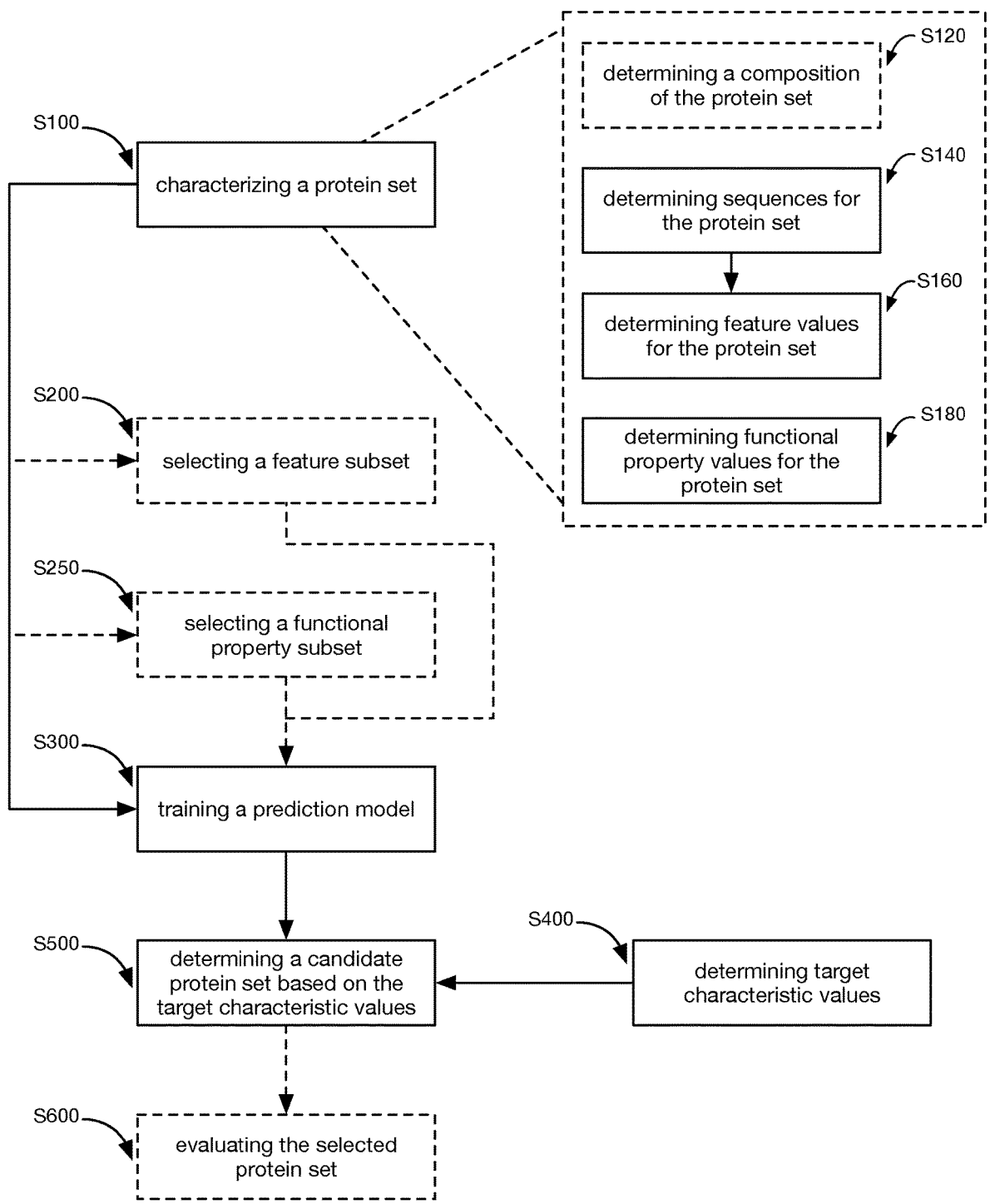
FIG. 1 is a schematic representation of a variant of the method.

As shown in FIG. 1, the method can include: characterizing a protein set S100, training a prediction model S300, determining target characteristic values S400, determining a candidate protein set based on the target characteristic values S500, and/or any other suitable steps.

In variants, the method can function to determine a candidate protein set with a desired set of functional property values (e.g., wherein the candidate protein set can be used in a replacement for a target food product). For example, the candidate protein set can be selected to replicate target functional property values of and/or replace: caseins, leather proteins (e.g., collagen, gelatin, etc.), meat proteins (e.g., myosin), and/or any other protein set. In variants, the method can optionally determine protein source sets that contain the candidate protein set.

2. EXAMPLES

Figure 14:
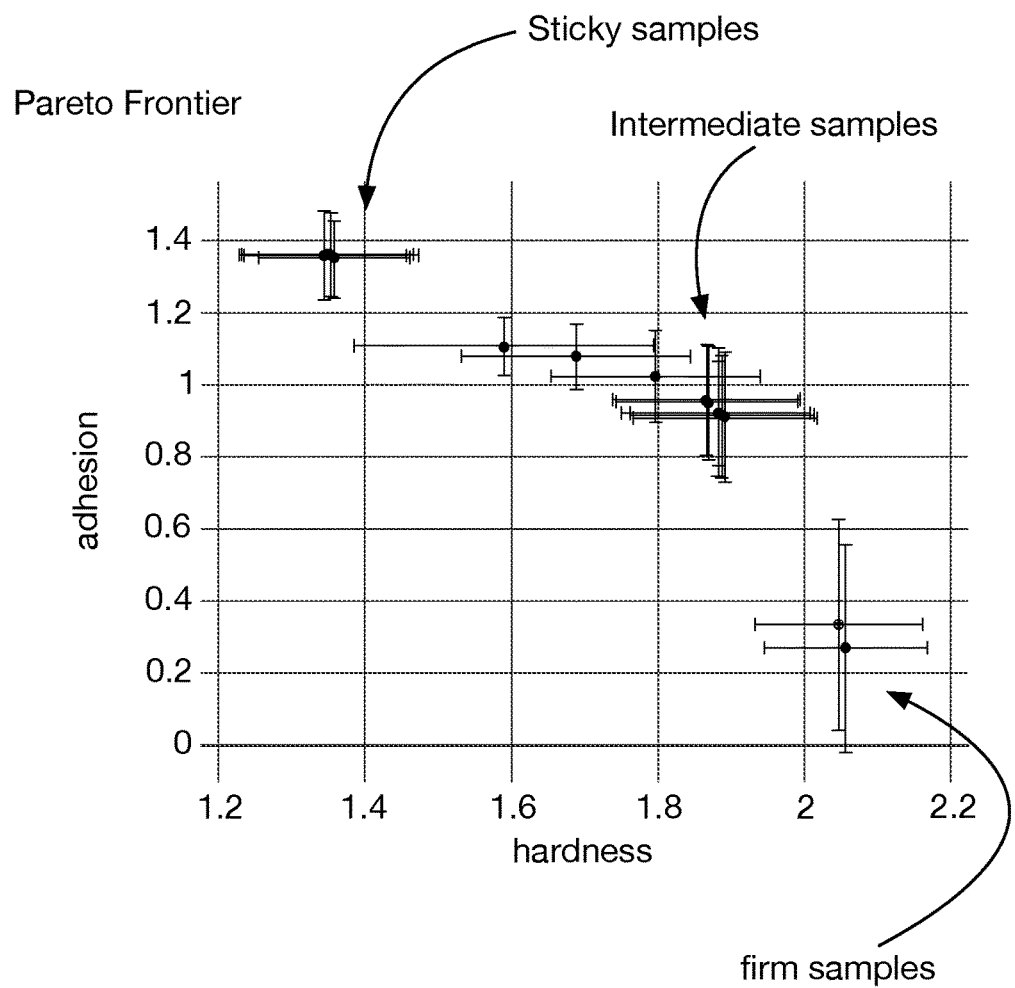
FIG. 14 depicts example functional property values for samples produced using phosphorylated proteins.

In an example, the method can include: predicting functional property values given a protein set and optionally a context (e.g., example shown in FIG. 14). In an illustrative example, the method can include: extracting feature values from the amino acid sequences for each of a set of protein sets, measuring functional property values for the set of protein sets, and training a prediction model to predict functional property values for a protein set based on feature values for the respective protein set. In a specific example, the prediction model can predict functional property values for the protein set based on aggregated feature values across individual proteins in the protein set. A protein set can optionally be associated with a composition (e.g., a relative and/or absolute concentration for each protein in the training protein set) and/or a context (e.g., manufacturing process parameters, protein modifications, etc.), wherein the composition and/or context can be inputs to the prediction model (e.g., separate vectors, concatenated to the protein set feature vector, used to weight the protein set feature vector, etc.).

In variants, measuring functional property values for a protein set can include manufacturing a sample matching the protein set composition using the process parameters and/or other context information, wherein the functional property values for the protein set are measured using assays. In a specific example, the target functional property values can be directly measured for a target product (e.g., a target food product).

In variants, the prediction model can be used to predict functional property values for each protein set in a candidate group, wherein the candidate group includes uncharacterized protein sets (e.g., without measured functional property data). A candidate protein set (e.g., including an associated composition and/or context) and/or a protein source with a high probability of producing the candidate protein set can then be selected from the candidate group based on a similarity between the predicted functional property values and target functional property values. Additionally or alternatively, a candidate protein set can be extracted from the prediction model (e.g., using an acquisition function), be predicted by a second model (e.g., a decoder), and/or otherwise determined.

3. TECHNICAL ADVANTAGES

Variants of the technology can confer one or more advantages over conventional technologies.

First, previous protein selection methodologies (e.g., to identify replacements for dairy and/or meat proteins) relied heavily on domain knowledge, previously researched protein alternatives, and laborious manual testing. Variants of the technology can utilize a computational approach to explore the extremely large and under-investigated protein space to identify candidate proteins that would not have otherwise been identified. For example, variants of the method can identify protein replacements based on the similarities between the amino acid sequence features (AA sequence features) of the candidate proteins and the target proteins (proteins to be replaced), and/or based on similarities between the predicted functional properties of the candidate proteins and the functional properties of the target product (e.g., food).

Second, variants of the technology can use a subset of features (e.g., subset of amino acid sequence features) which are likely to be important in influencing functional behavior. In a specific example, the functional property values are experimentally determined for protein sets (e.g., gelled mixtures of proteins) to capture important protein-protein interactions influencing function, and correlated with the feature values for the constituent proteins, wherein predictive features are selected for subsequent analysis based on the correlation. In a second specific example, lift analysis can be used (e.g., during and/or after training a prediction model) to select a subset of features with high lift. This feature selection can reduce computational complexity and/or enable human-interpretable annotation of the features.

Third, variants of the technology can reduce the need for experimental analysis of proteins to determine their candidacy potential. In an example, a large domain of available protein sets can be computationally analyzed (e.g., using featurization of their amino acid sequences) rather than experimentally analyzed to evaluate their potential to replicate functional properties of a target set of proteins. This analysis methodology can enable a much larger group of candidates to be considered than if experimental analysis of each protein set were required.

Fourth, variants of the technology can reduce the need for experimental analysis of potential protein sources by predicting whether a protein source (e.g., plant, plant component, etc.) will include sufficient amounts of a given protein or protein set, such as by using genetic analyses and/or evolutionary tree analyses.

However, further advantages can be provided by the system and method disclosed herein.

4. SYSTEM

Variants of the system can include a database and a set of models. The system functions to determine the functional properties for protein sets, determine which protein sets can produce a set of target functional properties, determine which protein sources can produce a target protein set, and/or be otherwise used.

Figure 2:
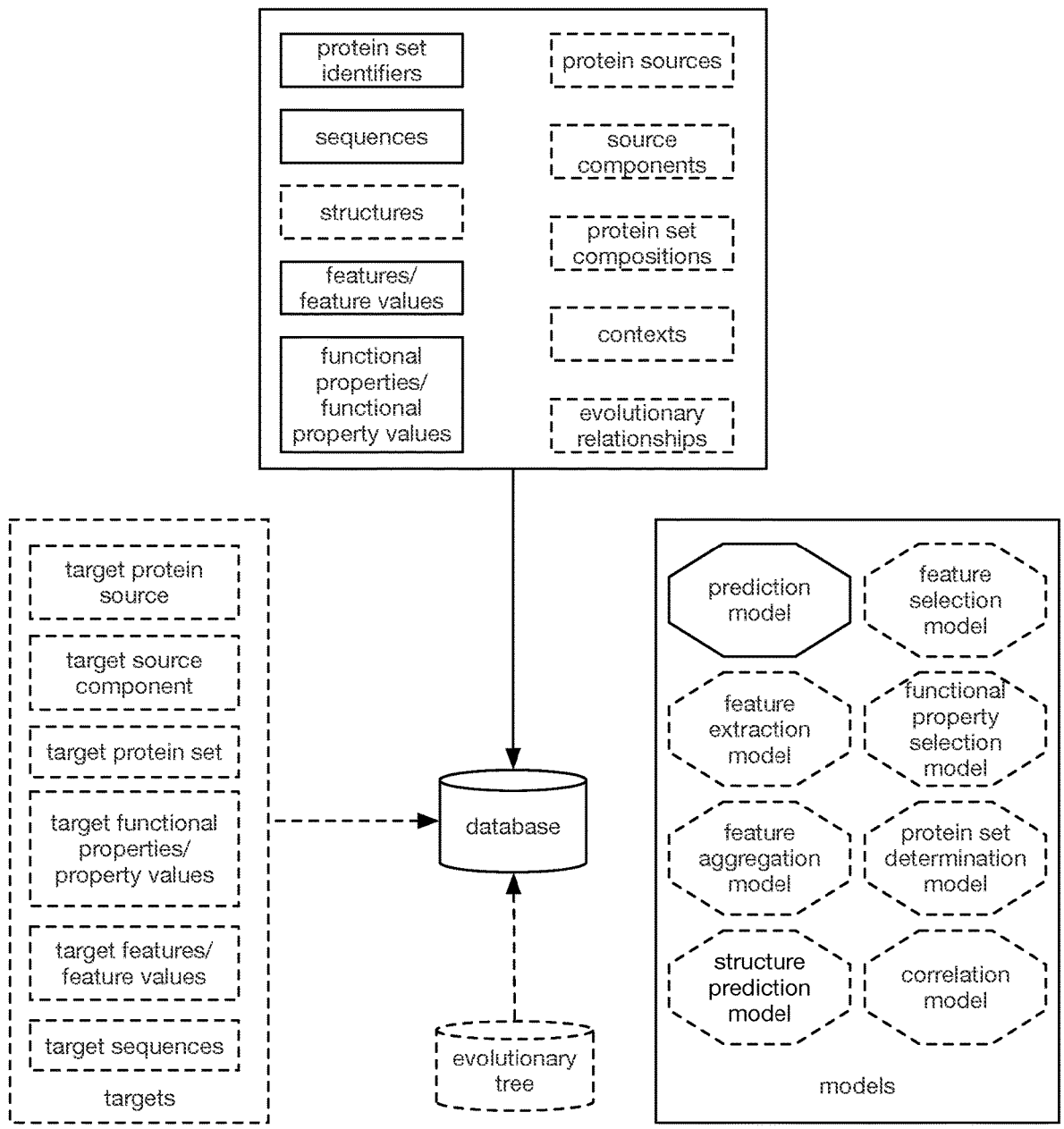
FIG. 2 is a schematic representation of a variant of the system.

An example of the system, including a database, is shown in FIG. 2. An example of the database is shown in FIG. 3. The database can include proteins, protein sets (e.g., protein set identifiers), protein set compositions (e.g., identification of proteins in the set, relative and/or absolute concentrations of proteins in the set, etc.), sequences, features, feature values, functional properties, functional property values, protein sources and/or source components, evolutionary relationships, contexts (e.g., process parameters, protein modifications, sample environment, etc.), and/or any other elements. The system can optionally include and/or interface with one or more third-party databases (e.g., a sequence database, a protein database, amino acid composition database, etc.). In a first example, elements stored in the system database can be retrieved from a third-party database. In a second example, the system database can be a third-party database.

A protein set can be an individual protein (e.g., a set of one, an individual protein within a larger set, etc.), multiple proteins (e.g., a mixture of proteins, proteins within a source and/or source component; within a gel, sample, product, solution, combination, and/or other mixture; within a food product; within a consumer product; etc.), a set of protein sets, and/or be otherwise defined.

The protein set can be from one or more protein sources (e.g., combination of protein sources), from one or more components of protein sources, be manually specified, and/or be otherwise determined. The protein source can be plant matter (e.g., processed and/or unprocessed plant matter), animal matter (e.g., milk such as cow milk, insects such as *Acheta domesticus*, meat, etc.), bacterium (e.g., naturally occurring, genetically modified, etc.), any organism (e.g., identified by a species name, a common name, etc.), a food product, a naturally-occurring protein source, a synthetic protein source, and/or any other entity and/or component (e.g., protein source component) thereof. The protein source component (e.g., the part of the source where the protein set can be derived) can be a nut, fruit, seed, legumes, stem, leaves, root, flower, stamen, muscle, carapace, and/or any other component of the associated source. The protein source can optionally be labeled (e.g., in the database) with one or more classifications (e.g., dairy, meat, non-dairy, non-meat, etc.). The protein source, source component, and/or the protein set can optionally be associated with an abundance metric (e.g., where the metric can assess the ease of accessing large quantities of the protein set for scaled use). The abundance metric can be: experimentally determined (e.g., measured), predicted (e.g., based on the abundance metrics for related protein sources), and/or otherwise determined. The abundance metric is preferably representative of a single protein's abundance within a protein source, but can alternatively be representative of a protein set's abundance within a protein source, be representative of the protein source's abundance, and/or represent other information.

The protein set can include all or a subset of proteins in the protein source and/or protein source component. In a first example, the protein set can include proteins above a concentration threshold in the protein source and/or source component (e.g., wherein the concentration threshold by weight can be 0.1%, 0.2%, 0.5%, 1%, 2%, 5%, 10%, 15%, 20%, 25%, 50%, etc.). In a second example, the protein set can include the most abundant (e.g., highest concentration) proteins in a protein source and/or a component of the protein source. In a specific example, the protein set can include a predetermined number of the most abundant proteins (e.g., wherein the predetermined number can be 1, 2, 3, 4, 5, 6, 7, 8, 9, 10, 15, 20, 50, etc.).

Plant matter can include: peas (e.g., pea flour, pea starch, etc.), rice (e.g., rice flour, glutinous rice flour, white rice flour, brown rice flour, etc.), fruits (e.g., citrus fiber), cassava (e.g., cassava flour), potato, cocoa beans, truffles, olives, coconut flesh, grape pomace, pumpkin (e.g., pumpkin seed), cottonseed, canola, sunflower, hazelnut, pistachio, almond, walnut, crude walnut, cashew, brazil nuts, hazelnut, macadamia nuts, pecan, peanut, hemp, oat, rice, poppy, watermelon (e.g., watermelon seed), chestnut, chia, flax, quinoa, soybean, split mung beans, aquafaba, lupini, fenugreek, kiwi, Sichuan pepper, mustard, sesame, sunflower seeds, algae, duckweeds (e.g., lenna), squash, chickpeas, pine nuts, peas, cassava, citrus (e.g., citrus fiber), fava bean (e.g., fava bean flower), grape (e.g., grape pomace), lima bean (e.g., lima bean paste), carrageenan; plants selected from the cucurbita, anacardium, cannabis, salvia, arachis, brassica, sesamun, legume, and/or other genuses; plants selected from the Anacardiaceae, Asteraceae, Leguminosae, Cucurbits, Rosaceae, Lamiaceae, and/or other family; a combination thereof, and/or any other plant matter. The plant matter may include major production oilseeds (e.g., soybean, rapeseed, sunflower, sesame, niger, castor, canola, cottonseed, etc.), minor production oilseeds (coconut, palm seed, pumpkin, etc.), and/or other crops or plant matter. The plant matter may exclude allergens (e.g., wheat, soy, peanut, etc.). The plant matter may include a single variety of plant matter, a mixture of various plant matter, include animal matter (e.g., insect matter, mammalian products, etc.), and/or include matter from any other source.

The protein source can be processed (e.g., lipid-removed, comminuted, separated into a solid and liquid component, mechanical processing, chemical processing, a protein powder derived from the plant matter, an extract from the plant matter, fermented, protein modifications, etc.) and/or unprocessed.

For example, the protein source can include a plant milk, powdered whole plant component (e.g., plant matter) in an aqueous solution, isolated plant protein (e.g., powder), and/or any other suitable source of protein. [0022] One or more proteins can be derived (e.g., extracted) from the protein source. The proteins can include protein isolates (e.g., solubilized protein isolates) extracted from the protein source. Protein isolates can include: proteins isolated using isoelectric precipitation (e.g., salting in, salting out, etc.), by collecting and optionally diluting a protein-rich solution (e.g., the supernatant obtained by spinning down a whole plant ingredient, such as a seed powder; residual obtained by removing at least a threshold proportion of insoluble solids from a plant milk, such as 50%, 75%, 80%, 90%, etc.; etc.), and/or otherwise obtained. The protein ingredient obtained from the plant matter can be substantially pure (e.g., wherein a single monomeric or multimeric protein represents at least 50%, 60%, 70%, 80%, 90%, and/or more than 90% of the overall protein content in the protein ingredient and/or the product), but can alternatively be impure (e.g., include more than 10%, 20%, 30%, 40%, 50%, 60% other proteins, etc.).

The proteins can include structured protein isolates (SPIs) produced using protein isolates. In a first example, SPIs can be produced by: obtaining a protein isolate mixture (e.g., a protein isolate solution) from a protein source; diluting the protein isolate mixture using a diluent; optionally separating the diluted protein isolate mixture (e.g., allowing sedimentation to occur, centrifuging, filtering, etc.); and collecting SPIs (e.g., an SPI mixture) and from the diluted protein isolate mixture (e.g., collecting the sediment, collecting all or part of a homogenous diluted lipid protein isolate mixture, etc.). The diluent can include water (e.g., deionized water), an aqueous solution (e.g., water, a mixture of water and other ingredients, etc.), an aqueous solution mixed (e.g., emulsified) with other ingredients, and/or any other diluent. The SPI mixture can include an aqueous component, a protein component, and/or other ingredients. The protein component can include protein isolates, SPIs, aggregates of SPIs, a combination thereof, and/or any other proteins. The protein concentration (by weight) in the SPI mixture can be between 0.01%-95% or any range or value therebetween (e.g., 1%-15%, 30%-50%, 44%, 40%, etc.), but can alternatively be less than 0.01% or greater than 95%.

The proteins can include: globulins (e.g., 2S globulins, 1S globulins, 7S globulins, conglutin, napin, sfa, edestin, amandin, concanvalin, vicilin, legumin, cruciferin, helianthinin, etc.), pseudoglobulins, globular proteins, prolamins, albumins, gluten, gliadin, conglycinin, hordein, phasolin, zein, olsosin, caloleosin, sterelosin, conjugated proteins (e.g., lipoprotein, mucoprotein, etc.), other storage proteins (e.g., seed storage proteins, vegetative storage protein, etc.), animal proteins (e.g., casein, insect proteins, etc.), and/or any other suitable protein or combination thereof. Proteins can optionally be modified (e.g., transglutaminase modifications, proteolytic modifications, glycosylation, glycation, phosphorylation, acylation, etc.) pre- or post-extraction from the protein source. The proteins (e.g., modified or unmodified) can optionally include SPIs, wherein protein isolate units (e.g., protein monomers arranged in an oligomeric complex such as a hexamer) can be arranged in: agglomerates, aggregates, micelles, stacks, and/or any other suitable higher-order arrangement (e.g., quaternary structure or higher). The SPI structure can be a sphere (e.g., a shell of protein isolate units, a shell or micelle with hydrophilic regions along the exterior and hydrophilic regions along the interior, etc.), an amorphous structure, and/or any other structure. The proteins can optionally include an aggregate of SPIs, wherein constituent SPIs can be arranged in: agglomerates, aggregates, micelles, stacks, and/or any other suitable higher-order arrangement. The proteins can include casein proteins, non-casein proteins, mammalian proteins, non-mammalian proteins, plant proteins, animal proteins, non-animal proteins, and/or any other proteins. For example, proteins in target protein sets can include casein proteins, mammalian proteins, and/or animal proteins, while proteins in candidate protein sets can substantially exclude casein proteins, mammalian proteins, allergen proteins (e.g., proteins from allergens, such as peanuts, soy, wheat, etc.), and/or animal proteins, and/or include plant proteins (e.g., exclusively include plant proteins). In a specific example, proteins in candidate protein sets can include casein, mammalian, and/or animal proteins below a threshold amount, wherein the threshold amount can be between 0.1%-10% or any range or value therebetween (e.g., 10%, 5%, 3%, 2%, 1%, 0.1%, etc.), but can alternatively be greater than 10% or less than 0.1%.

The protein set can be associated with a protein set composition and/or a total protein quantity (e.g., wherein the total protein quantity is an overall concentration or amount of proteins within a protein source and/or source component, an overall concentration or amount of proteins within a product, etc.). The protein set composition can include an identification of each protein in the set (e.g., a name or other identifier for each protein) and/or a concentration of each protein in the set. The concentration of a protein in the protein set can be an absolute concentration or a concentration relative to other proteins in the protein set. In examples, the concentration can be a percentage (e.g., by weight, by mass, by moles, etc.), a ratio, a proportion, an abundance, an amount (e.g., weight, mass, moles, etc.), a ranking (e.g., wherein each protein in the set is ranked relative to the other proteins based on concentration), and/or any other concentration metric. In an illustrative example, the composition of a first protein set can include a first protein (P1) at a concentration C1, and a second protein (P2) at a concentration C2; the composition of a second protein set can include the same proteins (P1 and P2) at difference concentrations C3 and C4, respectively. The protein set composition and/or the total protein quantity can be measured (e.g., using an assay), predetermined (e.g., manually specified), predicted (e.g., based on evolutionary relationships, using a prediction model, based on an amino acid composition, using a database, etc.), and/or otherwise determined. In a first specific example, a first protein source is associated with a first protein set with a known composition and a second protein source is associated with a second protein set with an unknown composition, wherein an evolutionary relationship (e.g., based on an evolutionary tree) between the first and second protein sources is used to predict the composition of the second protein set (e.g., using the assumption that certain proteins and/or protein concentrations would be similar between the first and second protein sets when the protein sources are evolutionarily close). In a second specific example, an overall composition of amino acids in a protein set is determined using an assay (e.g., LC/MS), and the composition of amino acids in each constituent protein are predicted based on the amino acid sequence for the respective constituent protein. In a third specific example, an overall composition of amino acids in a protein set and a composition of amino acids in each constituent protein are retrieved from an amino acid composition database (e.g., a third-party PseAAC database). A model (e.g., a regression) can be used to determine the concentration of each constituent protein within the protein set based on the overall amino acid composition (e.g., of the mixture) and the amino acid compositions for the constituent proteins.

The protein set can be associated with one or more sequences (e.g., one sequence for each individual protein in the set). Sequences can include amino acid sequences, genetic sequences (e.g., DNA sequence, RNA sequence, gene sequence, etc.), any molecular sequence, any protein sequence, and/or other genetic information. Sequences can be measured (e.g., using an assay), predetermined (e.g., manually specified), predicted (e.g., based on an evolutionary tree, using a prediction model, etc.), and/or otherwise determined.

The protein set can be associated with a context. The context can include: process parameters, protein modifications, sample environment, and/or any other information associated with the protein set and/or a sample (e.g., a food product, a gel, and/or any other product) containing the protein set. The context can be measured (e.g., using an assay), predetermined (e.g., manually specified), predicted, and/or otherwise determined.

The protein set can be associated with one or more protein structures (e.g., one structure for each protein, one structure for each protein-context combination, etc.). The protein structures can be measured, predicted (e.g., using protein structure prediction models, and/or otherwise determined.

Process parameters are preferably specifications prescribing the manufacturing of a sample containing the protein set (e.g., extracting the protein set from one or more protein sources, manufacturing the sample using the protein set, etc.), but can be otherwise defined. Process parameters can define: manufacturing specifications; the amounts thereof (e.g., ratios, volume, concentration, mass, etc.); temporal parameters thereof (e.g., when the input should be applied, duration of input application, etc.); and/or any other suitable manufacturing parameter. Manufacturing specifications can include: ingredients, treatments, and/or any other sample manufacturing input, wherein the process parameters can include parameters for each specification. Examples of ingredients can include: plant matter, proteins, lipids (e.g., fats, oils, etc.; isolated from plant sources; etc.), water, preservatives, acids and/or bases, macronutrients (e.g., protein, fat, starch, sugar, etc.), nutrients, micronutrients, carbohydrates, gums, vitamins, enzymes, emulsifiers, hydrocolloids, salts, chemical crosslinkers and/or non-crosslinkers, coloring, flavoring compounds, vinegar, mold powders, microbial cultures (e.g. cheese cultures, such as *Penicillium camemberti, Penicillium candidum, Geotrichum candidum, Penicillium roqueforti, Penicillium nalgiovensis, Verticillium lecanii, Kluyveromyces lactis, Saccharomyces cerevisiae, Candida utilis, Debaryomyces hansenii, Rhodosporidum infirmominiatum, Candida jefer, Cornybacteria, Micrococcus* sps., *Lactobacillus* sps., *Lactococcus, Staphylococcus, Halomonas, Brevibacterium, Psychrobacter, Leuconostocaceae, Streptococcus thermophilus, Pediococcus* sps., Propionibacteria culture, combinations thereof, etc.), carbon sources, any combination thereof, and/or any other ingredient. Examples of treatments can include: adjusting temperature, adjusting salt level, adjusting pH level, diluting, pressurizing, depressurizing, humidifying, dehumidifying, agitating, resting, adding ingredients, removing components (e.g., filtering, draining, centrifugation, etc.), adjusting oxygen level, brining, comminuting, fermenting, mixing (e.g., homogenizing), reactions (e.g., acylation, glycation, phosphorylation, etc.), structural adjustments (e.g., micellization, etc.) and/or other treatments. Examples of treatment parameters can include: treatment type, treatment duration, treatment rate (e.g., flow rate, agitation rate, cooling rate, etc.), treatment temperature, time (e.g., when a treatment is applied, when the sample is characterized, etc.), and/or any other parameters.

Protein modifications can include transglutaminase modifications, proteolytic modifications, glycosylation, glycation, phosphorylation, acylation, hydrolysis, and/or any other protein treatments. The modified proteins can be used as ingredients for a downstream product (e.g., dairy replicate), be used as a product (e.g., be sold as-is, be fermented using a cheese culture post-modification, etc.), and/or be otherwise used.

In a first embodiment, proteins (e.g., proteins containing nucleophilic residues, such as Lys, Ser, Thr, Cys, etc.; SPIs; etc.) can be acylated using fatty acyl anhydrides (e.g., caprylic anhydride; myristic acid; stearic acid; oleic acid; linoleic acid; etc.), yielding a fatty acylated protein (e.g., via an amide linkage, such as from Lys; ester linkage, such as from Ser; thioester linkage, such as from Cys; etc.) and a fatty acid. For example, the ratio between proteins and acyl anhydrides (e.g., by weight, by mass, by moles, etc.) can be between 1:1-1:4, but can alternatively be greater than 1:1 or less than 1:4. Unreacted fatty acyl anhydride can be quenched (e.g., with hydroxide and water, a base, a salt, etc.), yielding the corresponding fatty acid. The resultant fatty acylated protein and/or a sample therefrom can have increased lipid binding; increased hydrophobicity; increased gel strength; increased flow at elevated temperatures (i.e., melt); increased stretchiness; and/or other changed functional property values (e.g., values for texture, nutrition, etc.) relative to the unacylated protein or a sample therefrom. In variants, other carboxylic acid conjugation reagents (e.g., acyl chlorides, activated carboxylic acids, metal catalysts, etc.) can additionally or alternatively be used.

In a second embodiment, proteins (e.g., protein residues, surface-accessible nucleophilic residues, etc., SPIs, etc.) can be phosphorylated (e.g., using sodium trimetaphosphate). For example, nucleophilic residues (e.g., Ser, Thr, Lys) of the protein may attack sodium trimetaphosphate (STMP) and/or other reagents, resulting in a triphosphorylated protein which hydrolyses, releasing pyrophosphate to yield the phosphorylated protein. Examples of other phosphorylation reagents that can be used include: other trimetaphosphate salts; hexametaphosphate salts; tripolyphosphate salts; polyphosphate salts; nucleoside triphosphates, and/or other phosphorylation agents. In variants, phosphorylation can be performed using non-toxic (e.g., at relevant concentrations) catalysts, reagents, byproducts, and/or other substances. The resultant phosphorylated protein and/or a sample therefrom can have increased calcium binding (e.g., an increased calcium concentration in the sample); increased stretchiness;

increased flow at elevated temperatures (i.e., melt); increased solubility; increased hydrophobicity and/or hydrophilicity; decreased toxicity; decreased hydrophobicity and/or hydrophilicity; and/or other changed functional property values relative to an unphosphorylated protein and/or a sample therefrom.

In an example, the proteins (e.g., protein isolates, SPIs, dissolved and resuspended protein source substrate, etc.) can be suspended in a protein solution at a target protein concentration. The target protein concentration in the protein solution and/or the target protein concentration in a final mixture (e.g., including protein, acids/bases, phosphorylation reagent, calcium, etc.) is between 3%-50% or any range or value therebetween (e.g., 4-10%, 6%, 9%, greater than 6%, greater than 9%, 10-20%, 15%, etc.), but can alternatively be less than 5% or greater than 50%. In a specific example, the proteins are diluted to achieve the target concentration. The diluent can be water (e.g., deionized water), an aqueous solution (e.g., water, a mixture of water and other ingredients, etc.), and/or any other diluent. The protein solution can optionally be homogenized (e.g., for 30 s-10 min, 1 min, 2 min, 3 min, 5 min, any other time, etc.). The pH of the protein solution can be adjusted to a target pH, wherein the target pH is between 3-12 or any range or value therebetween (e.g., 3-5, 4, 5-7, 6, above 6, above 7, below 7, 10-11, 10, 10.5, 11, etc.), but can alternatively be less than 3 or greater than 12. A solution including a phosphorylation reagent (e.g., $Na_3(PO_3)_3$) can be added to the protein solution to achieve a target concentration in a final mixture (e.g., 20 mM-1000 mM, 100 mM-500 mM, 300 mM-400 mM, 80 mM, 150 mM, 250 mM, 350 mM, greater than 150 mM, greater than 80 mM, less than 80 mM, etc.). The resulting (intermediate) mixture can optionally be homogenized (e.g., for 30 s-10 min, 1 min, 2 min, 3 min, 5 min, any other time, etc.). The resulting mixture can be stirred for between 15 min-10 hrs or any range or value therebetween (e.g., 30 min-2 hrs, 1 hr, etc.), but can alternatively be stirred for less than 15 min or greater than 10 hrs. The stir rate can be between 100 rpm-10,000 rpm or any range or value therebetween (e.g., 300 rpm-1,000 rpm), but can alternatively be less than 100 rpm or greater than 10,000 rpm. The temperature while stirring can be between 10° C.-50° C. or any range or value therebetween (e.g., 20° C.-30° C., room temperature, etc.), but can alternatively be less than 10° C. or greater than 50° C. Calcium can optionally be added to the mixture (e.g., to bind calcium to the phosphorylated proteins, to enable the reaction to proceed forward, etc.) before or after phosphorylating agent addition. For example, a solution of calcium salts (e.g., $CaCl_2$)) can be added to the mixture to achieve a target concentration in a final mixture (e.g., 5 mM-40 mM, 20 mM-10000 mM, 20 mM-1000 mM, 80 mM, 100 mM, 140 mM, 240 mM, 300 mM, 400 mM, greater than 140 mM, less than 400 mM, etc.). The process parameters in this example can optionally achieve a sticky (e.g., increased adhesion, decreased hardness, etc.) texture in a sample produced using the phosphorylated proteins. An example is shown in FIG. 14. Additionally or alternatively, the texture of the sample can be hardened by increasing the amount of phosphorylating agent, decreasing the amount of calcium salts, decreasing the amount of protein in the starting protein solution, and/or decreasing the pH.

In examples, the phosphorylated proteins can optionally be collected, such as via centrifugation (e.g., collecting the sediment after centrifugation), filtration, precipitation, and/or other protein isolation methods, wherein the proteins can be used in all or parts of the method. The centrifugation speed can be between 500 rpm-20000 rpm or any range or value therebetween (e.g., 1,000 rpm-10,000 rpm, 5,000 rpm, etc.), but can alternatively be less than 500 rpm or greater than 20,000 rpm. The centrifugation time can be between 30 s-1 hr or any range or value therebetween (e.g., 5 min-30 min, 10 min, 20 min, etc.), but can alternatively be less than 30 s or greater than 1 hr. The proteins can optionally be resuspended after collection (e.g., washed) in a diluent (e.g., water). The ratio (by volume) between the collected protein and the diluent can be between 1:10-10:1 (e.g., 1:3, 1:2, 1:1, 2:1, 3:1, etc.), but can alternatively be less than 1:10 or greater than 10:1.

However, proteins can be otherwise phosphorylated.

In a third embodiment, proteins (e.g., protein residues, surface-accessible lysine residues, etc.) can be glycated. For example, lysine residues and/or other residues can covalently bond to sugars (e.g., via nucleophilic attack of an acyclic sugar's aldehyde), resulting in a glycated protein. In variants, glycation can be performed using non-toxic (e.g., at relevant concentrations) catalysts, reagents, byproducts, and/or other substances. The resultant glycated protein and/or a sample therefrom can have increased flow at elevated temperatures (e.g., melt); increased solubility; increased hydrophobicity and/or hydrophilicity; decreased toxicity; decreased hydrophobicity and/or hydrophilicity; and/or other changed functional property values relative to an unglycated protein and/or a sample therefrom.

Maillard glycation is conventionally achieved at high temperatures, which may result in protein denaturation and accelerates later stage reactions, including those resulting in advanced Maillard products (AMPs). AMPs can give rise to off-flavours and/or off-colours in a sample. In variants, the method can include catalyzing an initial glycation event (e.g., via base catalysis and/or acid catalysis), which can reduce or remove the need for high temperatures (e.g., in the initial and/or later stages).

In an example, glycating proteins can include: combing proteins and sugars in a solution; adjusting a pH of the solution; and adjusting a temperature of the solution.

The proteins (e.g., protein isolates, SPIs, dissolved and resuspended protein source substrate, etc.) and sugars can be combined in the solution (e.g., dissolved in a diluent such as water) at a target protein concentration and a target sugar concentration. The target protein concentration (e.g., by weight) can be between 5%-60% or any range or value therebetween (e.g., 10%-40%, 15%-35%, 15%-25%, 25%-35%, etc.), but can alternatively be less than 5% or greater than 60%. The target sugar concentration can be 5%-70% or any range or value therebetween (e.g., 20%-40%, 20%-30%, 30%-40%, etc.), but can alternatively be less than 5% or greater than 70%. Examples of sugars that can be used include: monosaccharides such as pentoses and hexoses (e.g., ribose, arabinose, xylose, glucose, galactose, fructose, etc.); disaccharides; oligosaccharides; polysaccharides; and/or any other sugars. The sugars can be plant-based, synthesized, and/or otherwise obtained. In variants, the sugar used can be selected based on its reactivity. For example, pentoses can be preferred to hexoses, which can be preferred to disaccharides, which can be preferred to oligosaccharides, which can be preferred to polysaccharides. However, the sugars can be otherwise selected.

The pH of the solution during glycation can be adjusted to a target pH. In a first specific example, all or parts of the glycation reaction can be performed at an acidic pH (e.g., an acid-catalyzed reaction). The target pH can be between 2-7 or any range or value therebetween (e.g., 3-6.5, 4-6, less than 6, etc.), but can alternatively be less than 2 or greater than 7. Examples of acid catalysts that can be used to adjust the pH can include: hydrochloric acid, Bronsted acids, Lewis acids, and/or other acids. In a second example, all or parts of the glycation reaction can be performed at a basic pH (e.g., a base-catalyzed reaction). The target pH can be between 7-11.5 or any range or value therebetween (e.g., 8-11, 9-10.5, 9-10, 10-10.5, greater than 8, greater than 9, etc.), but can alternatively be less than 7 or greater than 11.5. Examples of base catalysts that can be used to adjust the pH can include: sodium hydroxide, sodium bicarbonate, potassium bicarbonate, ammonium bicarbonate, and/or other bases. The acids and/or bases are preferably food safe, but can alternatively be not food safe.

The temperature of the solution can be adjusted to a target temperature for a target reaction time (e.g., wherein the temperature is maintained throughout the reaction time, wherein the temperature is adjusted during the reaction time, etc.). The target temperature can be between 10° C.-200° C. or any range or value therebetween (e.g., at or above 45° C., 40° C.-80° C., at or above 50° C., 55° C.-70° C., below 55° C., at room temperature, above room temperature, etc.), but can alternatively be less than 10° C. or greater than 200° C. The target temperature is preferably below the protein's denaturation point, but can alternatively be at or above the denaturation point. The target reaction time can be between 1 hour-1 week or any range or value therebetween (e.g., 5 hrs-10 hrs, 8 hrs, 24 hrs-48 hrs, 12 hrs-24 hrs), but can alternatively be less than 1 hour or greater than 1 week.

However, the proteins can be otherwise glycated.

In examples, modified proteins and/or a sample therefrom can have changed functional property values. The change in functional property value can be determined relative to a protein source, an unmodified protein, a reaction intermediary, a sample therefrom, and/or relative to any other compound or substance. Examples of changes can include: 5%, 10%, 30%, 50%, 80%, a range therebetween, over 80%, and/or any other increased or decreased proportion. In variants, one or more protein modification process variables can be selected, controlled, adjusted, and/or otherwise manipulated to achieve a target functional property value (e.g., target texture). Examples of variables that can be controlled include: the protein source; protein preprocessing methods (e.g., protein isolation techniques, etc.); protein configuration (e.g., protein isolates, structured or unstructured arrangement of protein isolates, etc.); reagents; protein and/or reagent concentrations; stoichiometric ratio between protein and reagents; reaction scale (i.e., mass of initial protein substrate, volume of solvent); reaction time; reaction temperature; reaction pH, quenching or not quenching; washing (e.g., removal of unreacted reactants and byproducts such as pyrophosphate, unreacted sugars, AMPs, etc.) or not washing; concentration (e.g., presence vs absence of acids, bases, and/or other ingredients; and/or other variables.

The sample environment can include: a composition of the sample (e.g., other macronutrients and their respective concentrations), sample structure information (e.g., sample matrix type; sample porosity; sample phase such as solid, liquid, and/or gaseous; etc.), pH level, temperature (e.g., temperature at which the functional properties for the sample would be measured), pressure, isoelectric point, and/or any other sample parameters.

Figure 4:
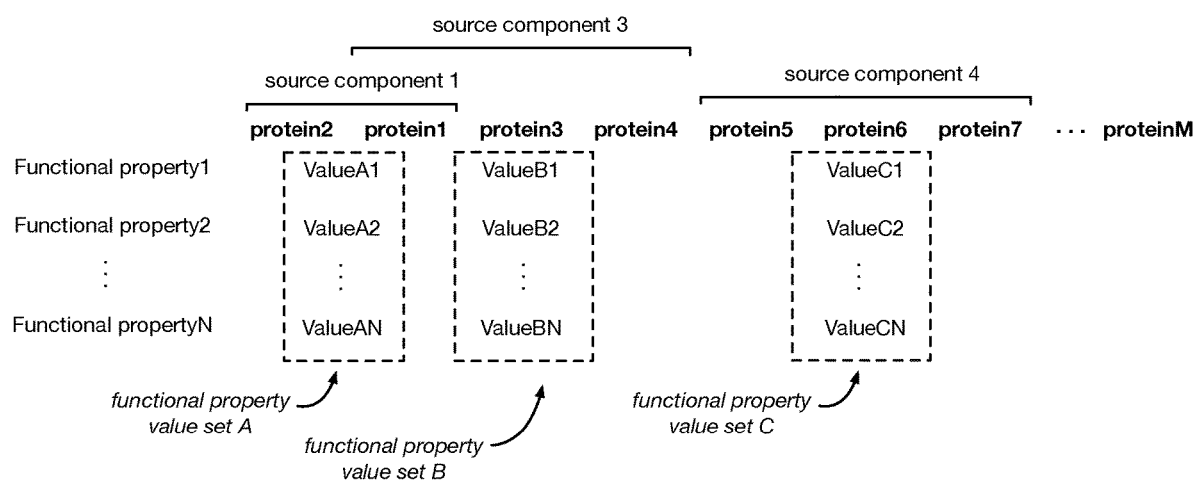
FIG. 4 depicts an illustrative example of functional property value sets associated with different source components and constituent proteins.

The protein set can be associated with values for one or more characteristics and/or can be uncharacterized (e.g., lack values for one or more characteristics). Characteristics can include: features, functional properties (e.g., an example of functional properties is shown in FIG. 4), functionalities (e.g., storage functionalities, breaking down sugar and/or any other molecule, enzyme functionalities, etc.), and/or any other characteristics.

Features are preferably sequence features (e.g., extracted from one or more amino acid sequences), but can alternatively be other protein characteristics (e.g., molecular features, physicochemical features, protein structure features, context features, etc.). Features can be human-interpretable (e.g., semantic features, where features represent specific properties, where the influence of a feature on functional properties is understood, etc.) or not human-interpretable (e.g., nonsemantic). Optionally, features can be annotated to provide human-interpretable context (e.g., by using an explainability or interpretability method applied to one or more models, etc.).

A feature set can include: all possible features, a subset of features (e.g., selected using dimensionality reduction, selected using a feature selection model, selected features based on correlation with specific functional properties, etc.), a user-defined set of features, weighted features, aggregated features, and/or any other suitable set of features. The features within the feature set can be: learned (e.g., using an autoencoder, using a deep learning model, etc.), handcrafted, and/or otherwise determined.

Figure 5A:
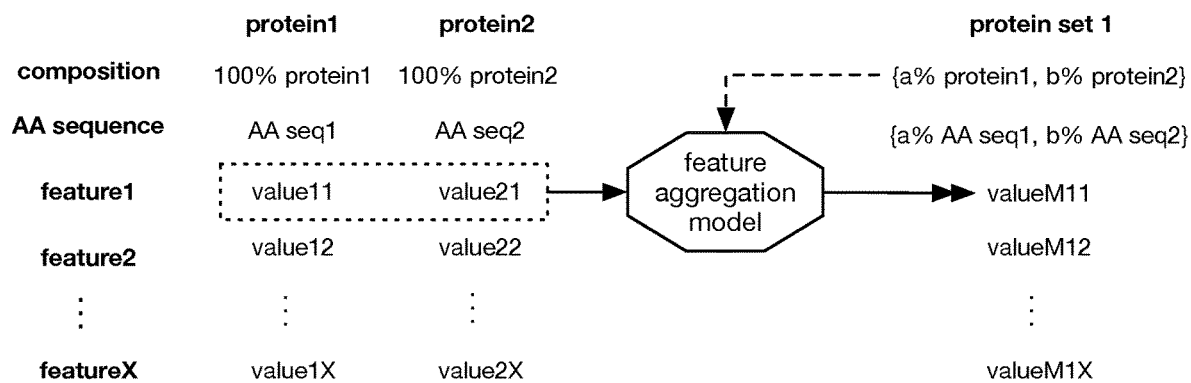
FIGS. 5A and 5B depicts illustrative examples of aggregating feature values for a protein set.
Figure 5B:
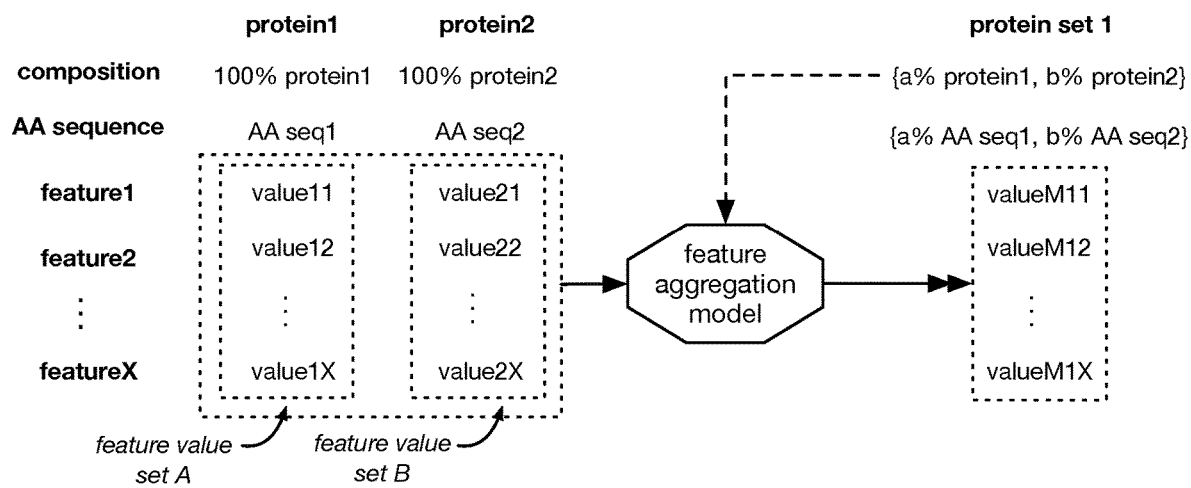

Each protein set can be associated with one feature value set (e.g., an aggregate feature value set), multiple feature value sets (e.g., one feature value set for each constituent protein, different feature value sets corresponding to different folding configurations, different feature value sets corresponding to different contexts, etc.), not have a feature value set, and/or be associated with any other feature value set. In an illustrative example, a feature value set is a feature value vector, wherein each element is a feature value for a feature in a feature set (e.g., a feature vector). In a first embodiment, each protein in the protein set is associated with a feature value set, wherein an aggregate feature value set (e.g., a representative feature value set) is determined for the protein set based on the feature values of the constituent proteins using a feature aggregation model (e.g., examples shown in FIG. 5A and FIG. 5B). In a second embodiment, a feature value set for the protein set can be directly determined (e.g., using a feature extraction model, using a machine learning model, etc.).

Features values can include and/or be extracted (e.g., using a feature extraction model) from: sequences (e.g., amino acid sequences, genetic sequences, etc.), measurements and/or other data, structures (e.g., primary, secondary, or tertiary structures that are known, measured, computer-generated, etc.), context, other feature values, and/or any other information. Examples of features can include: amino acid composition-based features, autocorrelation-based features, profile-based features, pseudo amino acid composition, sequence features (e.g., AA groups, active sites, binding sites, PTM sites, repeats, etc.), domain features, physicochemical features, domains, and/or any other feature. For example, features can include and/or be based on: k-mers; pseudo structure status composition (PseSSC); pseudo amino acid composition (PseAAC); composition, transition, and distribution (CTD); grand average of hydropathicity index (GRAVY); autocovariance; auto-cross covariance; top-n-gram; overall amino acid count; count and/or percentage of a specific amino acid; amino acid structure (e.g., amino acid subsequence organization within the amino acid sequence); charge (e.g., overall charge, charge distribution, charge at a given pH, etc.); acidity; hydrophilicity/hydrophobicity; functional groups; flexibility; instability; aromaticity; length; molecular weight; binding affinity;

active sites (e.g., count, structure, location, etc.); physicochemical and/or molecular features of amino acids; and/or any other feature.

However, features and/or feature values can be otherwise defined.

Functional properties can include macro functional properties, micro functional properties, nano functional properties, a combination thereof, other characteristics, and/or any other functional properties.

The set of functional property values for a protein set functions to define how the protein set and/or proteins in the protein set: behaves during sample preparation or cooking, influences the finished sample (e.g., in look, feel, taste, etc.), interacts with other molecules (e.g., secondary interactions, tertiary interactions, quaternary interactions, etc.), denatures (e.g., the denaturization point), folds, aggregates, other target functionalities, and/or any other behavior at the nano, micro, and/or macro scale (e.g., behaviors between the protein as a whole and the context or other proteins, etc.). Functional properties can include: nutritional profile (e.g., macronutrient profile, micronutrient profile, etc.), texture (e.g., texture profile, firmness, toughness, puncture, stretch, compression response, mouthfeel, viscosity, graininess, relaxation, stickiness, chalkiness, flouriness, astringency, crumbliness, stickiness, stretchiness, tearability, mouth melt, etc.), solubility, melt profile, smoke profile, gelation point, flavor, appearance (e.g., color, sheen, etc.), aroma, precipitation, stability (e.g., room temperature stability), emulsion stability, ion binding capacity, heat capacity, solid fat content, chemical properties (e.g., pH, affinity, surface charge, isoelectric point, hydrophobicity/hydrophilicity, chain lengths, chemical composition, nitrogen levels, chirality, stereospecific position, etc.), physiochemical properties, compound concentration (e.g., in the solid sample fraction, vial headspace, olfactory bulb, post-gustation, etc.), denaturation point, denaturation behavior, aggregation point, aggregation behavior (e.g., micellization capability, micelle stability, etc.), particle size, structure (e.g., microstructure, macrostructure, fat crystalline structure, etc.), folding state, folding kinetics, interactions with other molecules (e.g., dextrinization, caramelization, coagulation, shortening, interactions between fat and protein, interactions with water, aggregation, micellization, etc.), fat leakage, water holding and/or binding capacity, fat holding and/or binding capacity, fatty acid composition (e.g., percent saturated/unsaturated fats), moisture level, turbidity, interactions within the protein set (e.g., protein aggregation), properties determined using an assay tool, and/or any other properties. In examples, functional properties can include physicochemical and/or biochemical properties of amino acids and/or clusters of amino acids in each protein.

A functional property set can include: all possible functional property values, a subset of functional properties (e.g., selected using dimensionality reduction, selected using a functional property selection model, etc.), a user-defined set of functional properties, weighted functional properties, and/or any other suitable set of functional properties.

Functional property values sets can be associated with an individual protein, the entire set of proteins (e.g., a protein mixture; where each protein in the set is assigned the same functional property values, where functional property values are assigned to each protein based on individual protein concentrations within the set, etc.), a subset of the protein set (e.g., one or more proteins with the highest concentrations within the set), and/or be unassociated with the protein set (e.g., manually defined target functional properties). Each protein set can be associated with one functional property value set (e.g., wherein the functional property value set includes a value for each functional property in a functional property set), multiple functional property value sets (e.g., a protein set can be associated with different functional property value sets corresponding to different contexts), not have a functional property value set (e.g., uncharacterized), or be associated with any other functional property value set. In a specific example, a given protein can be associated with multiple functional property value sets, wherein each functional property value set corresponds to different protein sets that include the given protein. Functional property values can optionally include an uncertainty parameter (e.g., measurement uncertainty, determined using statistical analysis, etc.).

The functional property values can be determined experimentally (e.g., using an assay tool), determined via computer simulations, predicted (e.g., using a prediction model, based on the sample context, other functional properties, other inputs, etc.), and/or be otherwise determined. The functional property values can be: directly measured, analyzed and/or transformed data, features extracted from data (e.g., a data time series), and/or be otherwise determined.

However, functional properties and/or functional property values can be otherwise defined.

The system can optionally leverage one or more assays. Properties determined using an assay tool can optionally be and/or be used to determine any functional property value and/or feature value. Examples of assays and/or assay tools that can be used include: a differential scanning calorimeter (e.g., to determine properties related to melt, gelation point, denaturation point, etc.), Schrieber Test, an oven (e.g., for the Schrieber Test), a water bath, a texture analyzer, a rheometer, spectrophotometer (e.g., determine properties related to color), centrifuge (e.g., to determine properties related to water binding capacity), moisture analyzer (e.g., to determine properties related to water availability), light microscope (e.g., to determine properties related to microstructure), atomic force microscope (e.g., to determine properties related to microstructure), confocal microscope (e.g., to determine protein association with fat/water), staining (e.g., paired with computer vision models), laser diffraction particle size analyzer (e.g., to determine properties related to emulsion stability), polyacrylamide gel electrophoresis system (e.g., to determine properties related to protein composition), phos-tag acrylamide gel electrophoresis (e.g., to determine extent of phosphorylation), acrylamide gel electrophoresis (e.g., to determine extent of glycation), mass spectrometry (MS), gas chromatography (GC) (e.g., gas chromatography-olfactometry, GC-MS, etc.; to determine properties related to aroma/flavor, to determine properties related to protein composition, etc.), liquid chromatography (LC), LC-MS, fast protein LC (e.g., to determine properties related to protein composition), protein concentration assay systems, thermal gravimetric analysis system, thermal shift (e.g., to determine protein denaturization and/or aggregation behavior), ion chromatography, dynamic light scattering system (e.g., to determine properties related to particle size, to determine protein aggregation, etc.), Zetasizer (e.g., to determine properties related to surface charge), protein concentration assays (e.g., Q-bit, Bradford, Biuret, Lecco, etc.), particle size analyzer, sensory panels (e.g., to determine properties related to texture, flavor, appearance, aroma, etc.), capillary electrophoresis SDS (e.g., to determine protein concentration), spectroscopy (e.g., fluorescence spectroscopy, circular dichroism, etc.; to determine folding state, folding kinetics, denaturation temperature, etc.), absorbance spectroscopy (e.g., to determine protein hydrophobicity), CE-IEF (e.g., to determine protein isoelectric point/charge), total protein quantification, high temperature gelation, microbial cloning, Turbiscan, stereospecific analysis, and/or any other assay and/or assay tool. In an illustrative example, a sample made using the protein set can be stained (e.g., for lipids and proteins), imaged, and analyzed (e.g., using the image) to determine the sample's lipid and protein structure (e.g., treated as a functional property). The sample's can optionally be measured using GC-MS to determine the chemical composition of the sample.

The method can be used with one or more targets, wherein one or more candidate protein sets (e.g., analogous protein sets) can be determined based on the target (e.g., to replace a target protein set, to manufacture an analog for a target product, to identify a protein set with target characteristic values, etc.). Candidate protein sets can include: proteins found in a predetermined set of protein sources, proteins expressed by a predetermined set of species, genus, family, and/or other set of organisms, and/or other proteins. For example, candidate protein sets can include proteins found in plant-based sources (e.g., substantially excluding animal-based sources), naturally-occurring sources, genetically modified sources, synthetic sources, and/or any other suitable source. Target protein sets can include: a protein set to be replaced or replicated, or any other protein set. For example, target protein sets can include proteins found in animal-based sources (e.g., dairy sources).

The target can include one or more: target characteristics (e.g., features, functional properties, etc.), target characteristic values, target protein sets (e.g., a single protein set, a composition of protein sets, etc.), target sources, target products (e.g., target food products), and/or other targets. Examples of target food products include: dairy fats (e.g., ghee, other bovine milk fats, etc.), milk (e.g., cow milk, sheep milk, goat milk, human milk, etc.), cheese (e.g., hard cheese, soft cheese, semi-hard cheese, semi-soft cheese), yogurt, cream cheese, dried milk powder, cream, whipped cream, ice cream, coffee cream, other dairy products, egg products (e.g., scrambled eggs), additive ingredients, mammalian meat products (e.g., ground meat, steaks, chops, bones, deli meats, sausages, etc.), fish meat products (e.g., fish steaks, filets, etc.), any animal product, and/or any other suitable food product. In specific examples, the target food product includes mozzarella, burrata, feta, brie, ricotta, camembert, chevre, cottage cheese, cheddar, parmigiano, pecorino, gruyere, edam, gouda, jarlsberg, and/or any other cheese.

Figure 10:
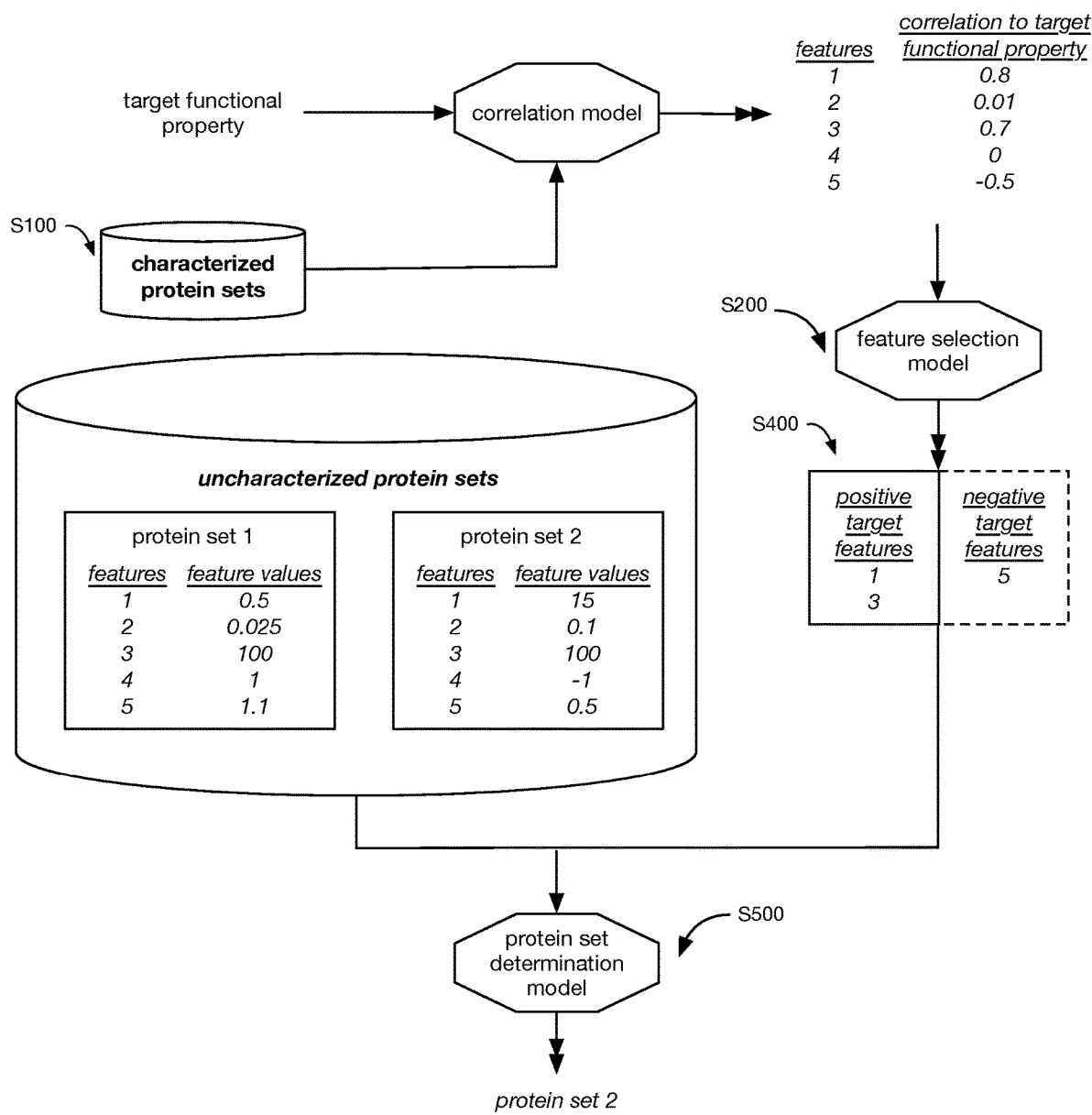
FIG. 10 depicts an embodiment of target determination.
Figure 11:
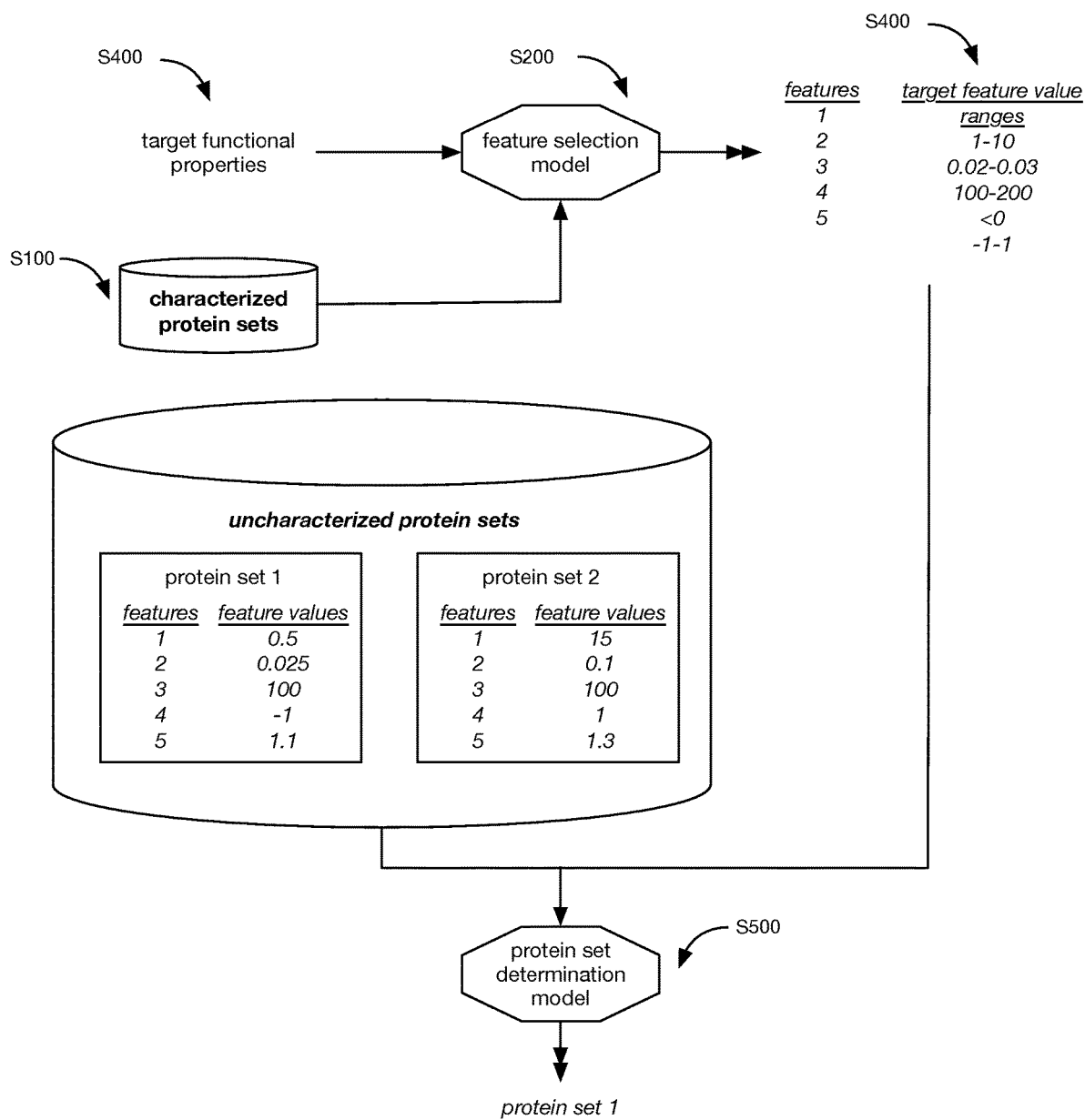
FIG. 11 depicts another embodiment of target determination.
Figure 12:
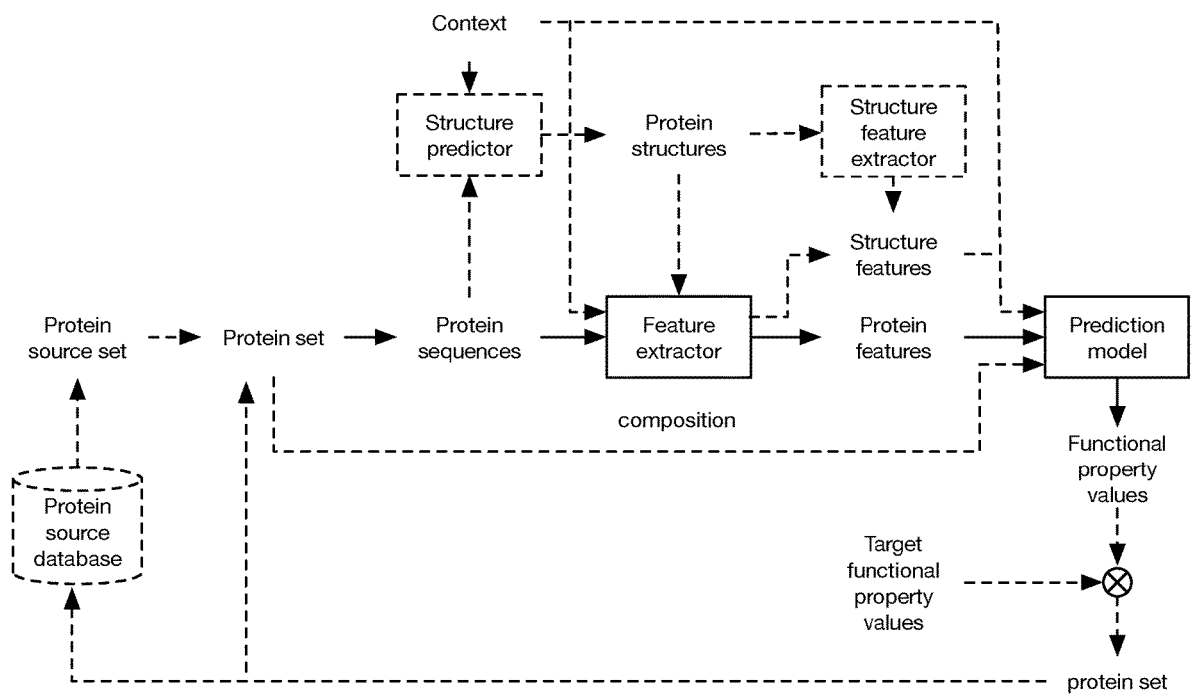
FIG. 12 depicts an example of predicting the functional properties for a protein set and optionally predicting a protein set or protein source set.

Target characteristic values can optionally be characteristic values for a target product and/or for a target protein set (e.g., associated with a target product). Target characteristic values can include a single value and/or ranges. A target can be: a single target (e.g., a single target characteristic value set for a given protein set) or aggregated targets (e.g., a vectorized set of feature values and/or functional property values aggregated across multiple protein sets, etc.). A target can be: a positive target (e.g., where positive target features are positively correlated with target functional properties; where desired characteristics are positive targets; etc.), or a negative target (e.g., where negative target features are negatively correlated with target functional properties; where undesired characteristics are negative targets; etc.); an example is shown in FIG. 10. In a first variant, the target characteristic values include desired feature values; an example is shown in FIG. 11. In a second variant, the target characteristic values include desired functional property values (e.g., associated with a target protein set, manually specified, etc.); examples shown in FIG. 10 and FIG. 12. However, the target can be otherwise defined.

The system can include one or more models, including feature extraction models, correlation models, feature selection models, functional property selection models, prediction models, protein set determination models, feature aggregation models, similarity models, structure prediction models, and/or any other model. Any model can include: regression, classification, neural networks (e.g., CNNs, DNNs, etc.), rules, heuristics, equations (e.g., weighted equations, etc.), selection (e.g., from a library), instance-based methods (e.g., nearest neighbor), regularization methods (e.g., ridge regression), decision trees, models used in Bayesian methods (e.g., Naïve Bayes, Markov), optimization methods, kernel methods, probability, deterministics, genetic programs, support vectors, and/or any other suitable method.

The models can include classical machine learning models (e.g., linear regression, logistic regression, decision tree, SVM, nearest neighbor, PCA, SVC, LDA, LSA, t-SNE, naïve bayes, k-means clustering, clustering, association rules, dimensionality reduction, etc.), neural networks (e.g., CNN, CAN, LSTM, RNN, autoencoders, deep learning models, etc.), ensemble methods, heuristics, and/or any other suitable model. The models can be scoring models, numerical value predictors (e.g., regressions), classifiers (e.g., binary classifiers, multiclass classifiers, etc.), and/or provide other outputs.

The models can be trained and/or learned, fit, predetermined, and/or can be otherwise determined. The models can be learned using: supervised learning, unsupervised learning, reinforcement learning, Bayesian optimization, positive-unlabeled learning, and/or otherwise learned. In specific examples, models can be trained using multiple-instance learning (MIL), learning to aggregate (LTA), and/or any other training approach. The models can be learned or trained on: labeled data (e.g., data labeled with the target label), unlabeled data, positive training sets (e.g., a set of data with true positive labels, negative training sets (e.g., a set of data with true negative labels), and/or any other suitable set of data.

The models can be specific to: functional properties, a protein set, a context, a target, and/or otherwise specific, or be generic. The feature extraction model can function to extract values for features for a protein set (e.g., for each protein in the set, for the protein set as a whole, etc.). The feature extraction model can output feature values based on molecular information inputs (e.g., sequences, measurements, data, structure, protein set composition, etc.), context, and/or other information. The feature extraction model can use: folding analysis, classifiers, the reduced alphabet approach, Markov models, statistical methods, n-gram analysis, autocovariance, auto-cross covariance, protein descriptor methods (e.g., PseSSC, PseAAC, CTD, GRAVY, etc.), any protein analysis methods, encoders (e.g., trained to encode the sequence to a shared latent space), and/or any other feature extraction technique. In a first example, the feature extraction model extracts handpicked features (e.g., wherein the feature extraction model is trained on a predetermined training value for the feature). In a second example, the feature extraction model can be adopted from another domain (e.g., be a linguistic feature model). In a third example, the feature extraction model can be a subset of the layers from a model trained end-to-end to predict another attribute (e.g., wherein the features can be learned features). In an illustrative example, the feature extraction model can be a subset of layers (e.g., the first several layers, feature extraction layers, intermediary layers, etc.) of a prediction model trained to predict functional property values from protein sequences, context, and/or other inputs (e.g., example shown in FIG. 14). However, the feature extraction model can be otherwise configured.

The extracted features for the protein set can be represented as one or more feature vectors, wherein each vector position can represent a different feature. In a first variant, a feature vector is determined for each protein within the set, wherein the feature value is determined based on the protein's sequence and optionally the protein's abundance or concentration within the protein set. Alternatively, the protein's abundance or concentration can be represented by a separate vector. In a second variant, a feature vector is determined for each protein set, wherein each feature's value is representative of the feature value for the protein set as a whole. In an example, the protein set feature vector is determined based on the feature's values for each protein in the protein set (e.g., wherein the different values for a given functional feature are aggregated, predicted, etc.), and optionally determined based on the respective protein's abundance within the protein set (e.g., weighted based on the respective protein's abundance within the set, etc.). However, the extracted features can be otherwise represented.

The optional feature aggregation model can function to aggregate feature values across proteins in a protein set. The feature aggregation model inputs can include: a feature value set (e.g., a feature value vector) for each protein in the protein set, a feature value set for each protein in a subset of the protein set, a protein set composition, context, and/or any other protein set information. The feature aggregation model outputs can include an aggregate feature value set (e.g., an aggregate feature value vector) for the protein set. The feature aggregation model can optionally interface with and/or be part of the prediction model (e.g., wherein the prediction model aggregates feature values).

The feature aggregation model can leverage classical or traditional approaches (e.g., heuristics, equations, etc.), leverage machine learning approaches (e.g., have learned parameters/weights, use MIL (multiple instance learning), use LTA learning, etc.), and/or be otherwise constructed. In a first embodiment, the feature aggregation model is a traditional or classical model. For example, the feature aggregation model can include a weighted combination (e.g., weighted average, etc.) of the feature value sets for individual proteins in the protein set, wherein the weights can be based on protein type, protein set composition (e.g., protein concentration, protein abundance in the protein set, etc.), and/or any other protein information. In a second embodiment, the feature aggregation model is a neural network. In a first example, the feature aggregation model includes a weighted combination of feature value sets for individual proteins in the protein set with optional interaction terms, wherein the weights and/or the interaction terms are learned parameters. In a second example, the feature aggregation model is the prediction model trained using MIL, wherein each instance is an individual protein with a respective concentration, each bag is a protein set, and bag labels are functional property values.

However, the feature aggregation model can be otherwise configured.

The prediction model can function to predict functional property values for a protein set. The prediction model can incorporate a correlation model, feature selection model, functional property selection model, feature aggregation model, and/or any other model. The prediction model inputs can include: a feature value set for each protein in the protein set (e.g., a feature value vector), a feature value set for the protein set (e.g., a feature value vector for the protein set as a whole, an aggregate feature value vector, etc.), protein set composition, context (e.g., parametrized into a context vector), correlation information (e.g., outputs from the correlation model), and/or any other protein set information. The prediction model outputs can include: a functional property value set and/or any other protein set information. The prediction model can include a single model and/or multiple models. When the prediction model includes multiple models, the models can be arranged in series, in parallel, as distinct models, and/or otherwise arranged. When the prediction model includes multiple models, the models can be trained separately (e.g., using distinct training data sets), trained together (e.g., using the same training data set, using different subsets of the same training data set, etc.), and/or otherwise trained.

Figure 8:
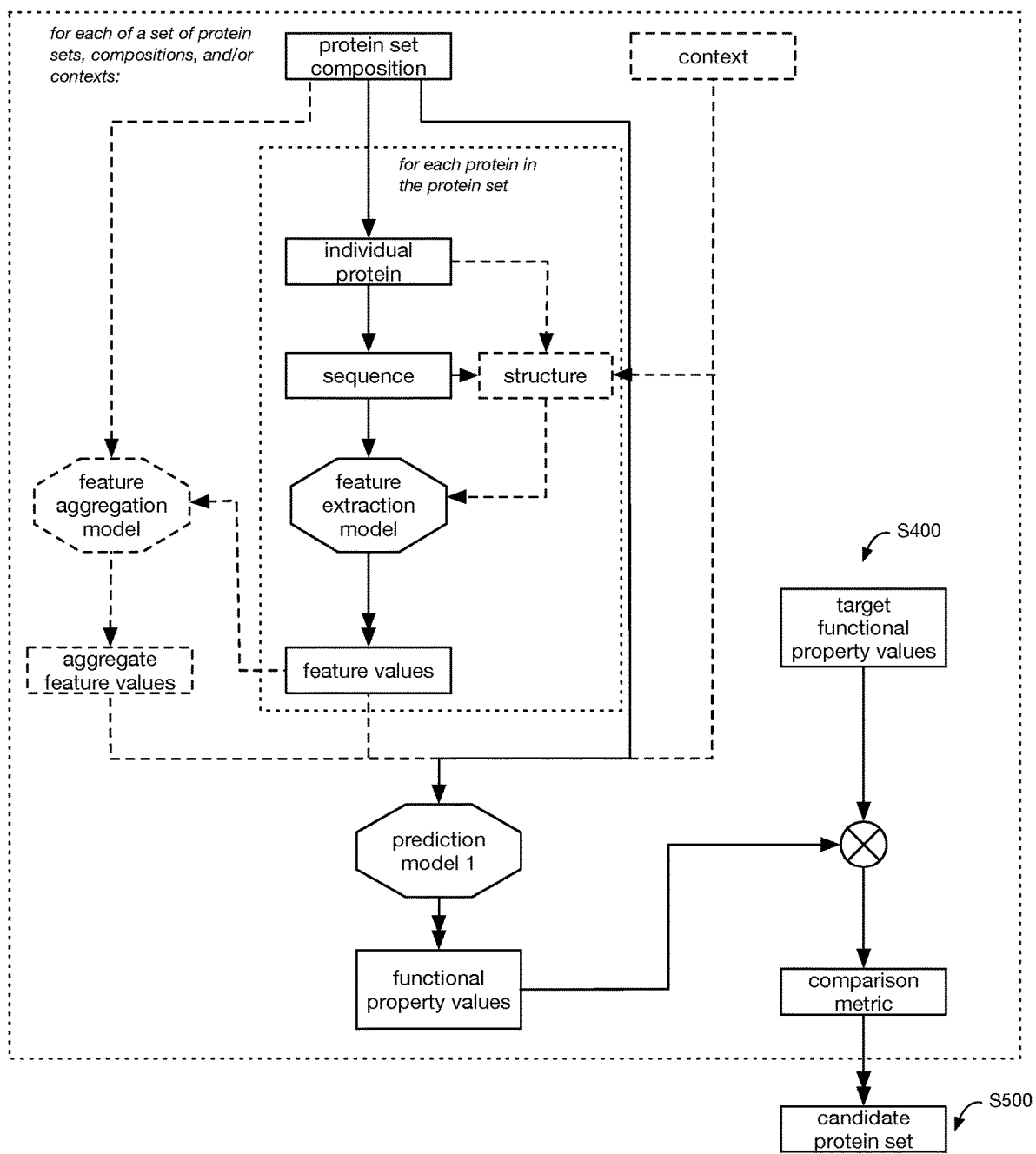
FIG. 8 depicts an example of determining a candidate protein set.
Figure 13:
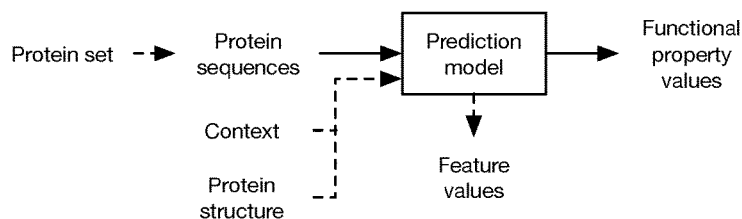
FIG. 13 depicts an example of predicting the functional properties for a protein set.

In a first variant, the prediction model outputs functional property values based on feature values associated with the protein set (e.g., feature values for individual proteins in the protein set and/or for the protein set as a whole). An example shown in FIG. 8. The model can optionally predict the functional property value based on the context; an example is shown in FIG. 13. For example, the context can be parametrized into a context vector, wherein the context vector can be appended to the protein set feature vector or provided as another input into the model. The model can predict a value for a single functional property (e.g., be a regression, classifier trained on a single functional property, etc.), values for multiple functional properties (e.g., be a multiclass classifier), and/or values for any other suitable set of functional properties.

In a second variant, the prediction model predicts functional property values based on protein sequences for the protein set. In an example, the prediction model can output a vector, wherein each vector position can represent a different functional property and the vector value can represent the predicted value for said functional property.

In a third variant, the prediction model predicts a functional property similarity score, indicative of the protein set's functional property similarity to a target sample's functional property, wherein the model can be analyzed (e.g., using an acquisition function) to determine which protein set (and/or feature vector) can produce a sample with functional properties that are closer to the target sample (e.g., using a Bayesian optimization technique).

In a fourth variant, the prediction model predicts the protein set that can produce the target functional property values, target feature values, and/or other target. The prediction model (and/or another model) can optionally predict the context (e.g., process parameters) needed to produce the target functional property values. The prediction model can predict: which proteins should be included in the protein set, the amount of each protein in the protein set, and/or other aspects of the protein set. In an example, the prediction model predicts a vector, wherein each vector position represents a different protein, and each value represents an amount of the respective protein. In a second example, the prediction model predicts a protein inclusion vector (e.g., which proteins should be in the set) and a protein amount vector (e.g., how much of the included proteins should be in the set). The two vectors can be predicted serially (e.g., protein inclusion vector first, then protein amount vector), at the same time, by the same model, by different models, and/or otherwise predicted.

However, the prediction model can be otherwise configured.

The optional protein set determination model (e.g., selection model) can function to determine a candidate protein set with characteristic values that closely match target characteristic values (e.g., the best/closest match, a match below a threshold, etc.). The protein set determination model inputs can include target characteristic values (e.g., target functional property values, target feature values, etc.), constraints (e.g., context constraints), the database, predicted characteristic values (e.g., predicted functional property values for each of a set of candidate protein sets), and/or any other information. The protein set determination model outputs can include: the candidate protein set (e.g., a candidate protein set selected from the database), the composition of the candidate protein set (e.g., the concentration for each protein in the set), the context for the candidate protein set, an ingredient (e.g., from which the candidate protein set can be derived; for use in product manufacture or target analog manufacture; etc.), and/or any other protein set information. The protein set determination model can use: comparison methods (e.g., matching, distance metrics, etc.), thresholds, optimization methods, regression, selection methods, classification, neural networks (e.g., CNNs, DNNs, etc.), clustering methods, rules, heuristics, equations (e.g., weighted equations, etc.), and/or any other methods. For example, the protein set determination model can search the database for a candidate protein set and/or determine a new protein set based on the target characteristics. The protein set determination model can optionally interface with and/or be part of the prediction model, the similarity model, and/or any other model. In a specific example, the protein set determination model can interface with and/or include the prediction model, wherein functional property values are predicted for each of a set of protein sets (e.g., uncharacterized protein sets) using the prediction model. The protein set determination model can then select a candidate protein set based on a comparison between the predicted functional property values and target functional property values (e.g., using the similarity model). In another example, the protein set determination model can determine the target feature values for a target protein set and identify a candidate protein set based on a comparison (e.g., the similarity) between the respective feature values (for the candidate protein set) and the target feature values, and/or a comparison (e.g., dissimilarity) between the respective feature values and a set of negative target feature values (e.g., feature values from protein sets to avoid).

However, the protein set determination model can be otherwise configured.

The optional correlation model can function to determine the correlation, interaction, and/or any other association between features and functional properties. For example, a correlation model can determine correlations between features and functional properties. However, the correlation model can determine correlations between any first set of features and/or functional properties and any second set of features and/or functional properties.

The correlation model inputs can include features (e.g., specifying a subset of features for correlation), feature values (e.g., individual protein feature values and/or aggregate feature values), sequences, functional properties (e.g., specifying a subset of functional properties for correlation), functional property values (e.g., where the feature values and/or functional property values are associated via common protein sets in the database), context, protein set compositions, the database, and/or any other information. The correlation model outputs can include a mapping between features (e.g., features, feature values, ranges of values, etc.) and functional properties (e.g., functional properties, functional property values, ranges of values, etc.), wherein the mapping can include: correlation coefficients (e.g., negative and/or positive), interaction effects (e.g., negative and/or positive, where a positive interaction effect can represent an increased significance effect of feature A on a functional property when in the presence of feature B), an association, and/or other correlation metric. The correlation model can use: classifiers, SVMs, ANNs, RF, conditional random field (CRF), K-nearest neighbors, statistical methods, and/or any other method.

In variants, the mapping between features and functional properties can be an association between features and functional properties (e.g., an autocorrelation feature is correlated with stretchability), feature values and/or ranges thereof with functional properties (e.g., a first range of autocorrelation values is correlated with stretchability, while a second range of autocorrelation values is correlated with spreadability, etc.), features with functional property values and/or ranges thereof, feature values and/or ranges thereof with functional property values and/or ranges thereof (e.g., autocorrelation values are correlated with spreadability values), combinations of features with combinations of functional properties (e.g., including interaction effects between features), combinations of feature values with combinations of functional property values, and/or any other association.

The correlation model can optionally be trained on a set of characterized protein sets (e.g., characterized with feature values, functional property values, etc.). In variants, the correlation model can identify similar and/or divergent feature values (e.g., calculating an implicit and/or explicit similarity measure) between protein sets and correlate those features to functional properties. For example, features with differing values (e.g., across protein sets) can be mapped to the functional properties with differing values (e.g., across the same protein sets). In a first specific example, a first feature is mapped to meltability when the feature values for two protein sets are substantially similar (e.g., within a threshold) except for the first feature's values, and the functional property values for the two protein sets are substantially similar except for the meltability values. In a second specific example, feature value differences (e.g., sequence differences determined using a sequence alignment method, a classifier, etc.) between related proteins (e.g., where a relation is determined using an evolutionary tree) can be correlated with differences in the respective functional property values.

However, the correlation model can be otherwise configured.

The optional feature selection model can function to select a subset of features (e.g., to reduce feature dimensions, to select features likely influencing functional properties, etc.). The feature selection model inputs can include: features, feature values, functional properties, functional property values, target characteristic values, correlation information (e.g., outputs from the correlation model, correlation coefficients, interaction effects, etc.), the database, and/or any other protein set information. The feature selection model outputs can include: a feature subset, target features (e.g., positive and/or negative targets), and/or any other features. The feature selection model can use: supervised selection (e.g., wrapper, filter, intrinsic, etc.), unsupervised selection, recursive feature selection, lift analysis (e.g., based on a feature's lift), any explainability and/or interpretability method (e.g., SHAP values), and/or with any other selection method. The feature selection model can be a correlation model (and/or vice versa), can include a correlation model (and/or vice versa), can take correlation model outputs as inputs (and/or vice versa), be otherwise related to a correlation model, and/or be unrelated to a correlation model.

The feature selection model can optionally be trained to select relevant features for functional property value prediction. For example, the training target can be a subset of features with high (positive and/or negative) interaction effects and/or correlation with functional properties (e.g., a correlation coefficient for a feature and/or feature set given a target functional property, interaction coefficients for features, whether an expected correlation and/or interaction was validated and/or invalidated in S600, etc.). However, the feature selection model can be otherwise trained.

However, the feature selection model can be otherwise configured.

The optional functional property selection model can function to select a subset of functional properties (e.g., to reduce dimensions, etc.). The functional property selection model inputs can include: functional properties, functional property values, target characteristic values, correlation information (e.g., outputs from the correlation model, correlation coefficients, interaction effects, etc.), the database, and/or any other protein set information. The functional property selection model outputs can include: a functional property subset, target functional properties (e.g., positive and/or negative targets), and/or any other functional properties. The functional property selection model can use: supervised selection (e.g., wrapper, filter, intrinsic, etc.), unsupervised selection, recursive feature selection, lift analysis (e.g., based on a functional property's lift), any explainability and/or interpretability method (e.g., SHAP values), and/or with any other selection method. The functional property selection model can be a correlation model (and/or vice versa), can include a correlation model (and/or vice versa), can take correlation model outputs as inputs (and/or vice versa), be otherwise related to a correlation model, and/or be unrelated to a correlation model.

However, the functional property selection model can be otherwise configured.

The optional similarity model can function to compare two sets of characteristic values. The similarity model inputs can include candidate protein set characteristic values, target characteristic values, and/or any other information. The similarity model outputs can include a comparison metric. The similarity model can use: comparison methods (e.g., matching, distance metrics, etc.), thresholds, optimization methods, regression, selection methods, classification, neural networks (e.g., CNNs, DNNs, etc.), clustering methods, rules, heuristics, equations (e.g., weighted equations, etc.), and/or any other methods. The comparison metric can be qualitative, quantitative, relative, discrete, continuous, a classification, numeric, binary, and/or be otherwise characterized. The comparison metric can be or include a distance, difference (e.g., vector of differences between values for each characteristic, vector of squared differences between values for each characteristic), ratio, regression, residuals, clustering metric (e.g., wherein multiple samples of the candidate and/or target protein sets are evaluated, wherein multiple candidate and/or target protein sets are evaluated, etc.), a statistical measure, and/or any other comparison measure. In an example, the comparison metric is a distance in feature space (e.g., wherein a characteristic value set is an embedding in the feature space). In a specific example, the comparison metric is low (e.g., the candidate protein set is similar to the target product/protein set) when the candidate protein set characteristic values are near (in feature space) positive target characteristic values and/or far from negative target characteristic values. However, the similarity model can be otherwise configured.

The optional structure prediction model functions to predict the protein folding structure, given the context. The resultant structure can be parametrized and used to determine the protein set feature values, used to determine the functional property values, or otherwise used. Examples of structure prediction models that can be used include: AlphaFold, I-TASSER, HHpred, and/or any other suitable protein structure prediction model.

However, the models can be otherwise defined.

The system can optionally include an evolutionary tree (e.g., representing evolutionary relationships or distances between protein sources, protein sets, etc.). The evolutionary tree and/or evolutionary distances based on the evolutionary tree can be predetermined (e.g., where the evolutionary tree is stored in the system database and/or a third-party database), be retrieved (e.g., for each source in the database), and/or be otherwise determined. The evolutionary tree can be used to identify features, facilitate protein and/or protein set selection, discover a protein source component for a given protein set, and/or be otherwise used. In an example, the evolutionary tree can be traversed to identify candidate protein sources and/or protein source components (e.g., source components that are more commercially feasible) that might have similar protein sets to a given protein source.

5. METHOD

As shown in FIG. 1, the method can include: characterizing a protein set S100, training a prediction model S300, determining target characteristic values S400, determining a candidate protein set based on the target characteristic values S500, and/or any other suitable steps. The method can optionally include selecting a feature subset S200, selecting a functional property subset S250, evaluating the candidate protein set S600, and/or any other suitable steps.

The method can be performed once (e.g., for a given target), iteratively (e.g., to train one or more models, to iteratively improve determination of a candidate protein set, etc.), concurrently with data generation (e.g., where a database of characterized and/or uncharacterized sources is iteratively updated while one or more protein set determination events are occurring), and/or at any other suitable frequency. All or portions of the method can be performed in real time (e.g., responsive to a request), iteratively, asynchronously, periodically, and/or at any other suitable time. All or portions of the method can be performed automatically, manually, semi-automatically, and/or otherwise performed. All or portions of the method can be performed during training and/or inference (e.g., prediction).

All or portions of the method can be performed by one or more components of the system, by a user, by a computing system, and/or by any other suitable system. The computing system can include one or more: CPUs, GPUs, custom FPGA/ASICS, microprocessors, servers, cloud computing, and/or any other suitable components. The computing system can be local, remote, distributed, or otherwise arranged relative to any other system or module.

Characterizing a protein set S100 functions to determine abstracted characterizations (e.g., feature values, functional property values, etc.) of the protein set, wherein the characterizations can be used to train the prediction model and/or any other model (e.g., to generate training data), to determine correlations between features and functional properties, to expand the database, and/or for any other downstream functionality. S100 can be performed before S400 and/or at any other time.

In a first variant, the protein set is characterized as a whole (e.g., where characteristic values are determined for and/or associated with the protein set as a unit). In a second variant, the protein set is characterized based on the characteristic values (e.g., feature values, functional property values, etc.) of the constituent proteins. In a first example, each constituent protein is individually characterized, and the mixture characterization is determined based on the individual characterizations (e.g., a set including the individual characteristic values, aggregated individual characteristic values, characteristic values weighted based on the concentration of the constituents in the protein mixture, characteristic values weighted based on a relative importance for a constituent protein in influencing functional properties, etc.). In a specific example, the protein set characterization can be determined using a model (e.g., the feature aggregation model, a machine learning model, etc.) that determines protein set characteristic values based on the individual characterizations of the constituent proteins. In a second example, a subset of proteins in the mixture are assigned characteristic values (e.g., only the highest concentrated protein(s) are assigned feature values and/or functional property values, proteins having a concentration percent value higher than a threshold, etc.).

Characterizing a protein set can include: optionally determining a composition of the protein set (e.g., S120), determining sequences for the protein set (e.g., S140), determining feature values for the protein set (e.g., S160), determining functional property values for the protein set (e.g., S180), and/or optionally determining a functionality (e.g., impact on functional properties, interaction with other molecules, structural functions, etc.) of the protein set (e.g., using machine learning annotation, using a correlation model, using explainability and/or interpretability methods, etc.). In variants, S120, S140, S160, and S180 are performed for training protein sets, while only S120, S140, and S160 are preformed for candidate protein sets. However, S100 can be otherwise performed.

Characterizing the protein set can optionally include manufacturing a sample using the protein set (e.g., wherein the manufacturing process is defined based on a context associated with the protein set), wherein all or parts of S100 are performed for the sample. The sample can optionally be processed prior to, during, or after, performing any assay (e.g., using dilution, centrifugation, dehydration, lyophilization, reconstitution, concentration methods, etc.).

Determining a composition of the protein set S120 functions to identify each protein and/or the concentration of each protein in the set (e.g., a concentration for each protein within the protein set, a concentration of each protein within a sample containing the protein set, etc.). In a first variant, the composition can be manually or automatically specified (e.g., for a candidate protein set). In a second variant, the composition of the protein set can be measured (e.g., using mass spectrometry proteomics, a Bradford assay, capillary Electrophoresis SDS, and/or any other assay). For example, a sample can be manufactured using the protein set, wherein the protein set composition in the sample is measured using one or more assays and/or assay tools. In a specific example, a total protein quantification and individual protein abundances can be measured for the sample, wherein the concentration for each protein in the sample is based on the total protein quantification and individual protein abundances. In a third variant, the composition can be inferred using bioinformatics (e.g., machine learning techniques applied to codons), genomics, transcriptomics, and/or other protein expression prediction techniques. However, the composition can be otherwise determined.

The protein concentrations (e.g., mol %, wt %) can be used to identify the most abundant proteins in the set, to weight variables (e.g., features), used in downstream analyses to determine proteins that have a disproportionate effect on functional properties relative to their concentration, and/or otherwise used. For any part of the method, a protein set and/or data associated with a protein set can be adjusted based on the protein composition. In a first example, a subset of the protein set is determined (e.g., to represent the complete protein set), wherein the subset includes the highest prevalence proteins in the set. In a first specific example, proteins that occupy a proportion of the protein set above a threshold percentage are selected as the subset, wherein the threshold percentage can be between 0.5%-50% or any range or value therebetween (e.g., 1%, 2%, 5%, 10%, 15%, 20%, 25%, 50%, etc.), but can alternatively be less than 0.5% or greater than 50%. In a second specific example, proteins with an overall concentration in the sample above a threshold percentage (e.g., mol %, wt %) are selected as the subset, wherein the threshold percentage can be between 0.05%-20% or any range or value therebetween (e.g., 0.1%, 0.2%, 0.5%, 1%, 2%, 5%, 10%, 15%, etc.), but can alternatively be less than 0.05% or greater than 20%. In a third specific example, a threshold number of the highest prevalence proteins are selected for the subset, wherein the threshold number can be between 1-100 or any range or value therebetween (e.g., 2-10, 5, 10, 15, etc.), but can alternatively be greater than 100. In a third specific example, proteins having a certain set of characteristics (e.g., binding affinity, adsorption affinity, etc.) that enable easy extraction and/or purification can be selected as the subset. In a second example, data associated with a protein set can be weighted based on the proportions of each constituent protein.

However, the protein set composition can be otherwise determined.

Determining sequences for the protein set S140 functions to determine information for feature extraction (e.g., for sequence-based features) and/or to directly determine feature values (e.g., where the feature values are sequences). Sequences can be measured (e.g., using an assay), retrieved (e.g., from a third-party database), and/or otherwise determined. Determining sequences can optionally include determining secondary information associated with the sequences (e.g., protein structure information, metadata, etc.). In a first variant, a sequence is preferably determined for each individual protein in the protein set (e.g., retrieved from a databased, determined using protein sequencing, etc.), but can alternatively be determined for a subset of proteins in the protein set, be determined directly for the protein set as a whole, and/or be otherwise determined. However, sequences for the protein set can be otherwise determined.

Determining feature values for the protein set S160 functions to computationally identify characterization values (e.g., molecular property values) of the protein set. S160 can be performed one or more times for each protein in a protein set, one or more times for each protein in a subset of the protein set (e.g., for the highest prevalence proteins in the protein set), one or more times for each protein set (e.g., iterating through a database), after S200 (e.g., where feature values for a protein set are determined for the features selected in S200), and/or at any other suitable time. The feature values can optionally be a feature value vector (e.g., wherein each element of the vector is a feature value for a feature in a feature set).

Feature values are preferably determined using the feature extraction model, but can alternatively be otherwise determined. In a first variant, feature values can be computationally determined. In a first example, feature values can be extracted from sequences (e.g., amino acid sequences). In a second example, feature values can be based on a computationally-determined protein charge and/or charge distribution. In a third example, feature values can be determined based on a modeled folding pattern (e.g., a likely protein folding pattern). In a fourth example, context feature values can be determined based on context information (e.g., extracted from ingredient lists, treatments, protein modifications, etc.) and optionally the protein sequences. In a second variant, feature values can be measured and/or extracted from measurements (e.g., experimentally determined using assays). In a third variant, feature values can be determined using a simulation (e.g., protein folding simulation, protein functionality simulation, protein interaction simulation, etc.). In a fourth variant, feature values can be retrieved from a database (e.g., a third-party database, the system database, etc.). In a fifth variant, a first subset of feature values can be determined using a first feature extraction model while the remaining feature values are determined using a second feature extraction model (e.g., using values from the first feature subset, using other information, etc.).

Feature values can be determined using one or more of the variants. In a first example, feature values can be computationally determined and subsequently validated and/or updated using measurements (e.g., values for water binding capacity can be estimated based on computationally determined charge distribution and/or folding pattern, then subsequently tested using centrifugal compression). In a second example, the amino acid sequence for each protein of the protein set (e.g., for a subset of the protein set including the highest prevalence proteins) can be retrieved from a third-party database, then feature values can be subsequently extracted based on the retrieved sequences. In a third example, context feature values can be determined based on context information retrieved from the database, and sequence feature values can be determined using a feature extraction model.

S160 can optionally include aggregating feature values across individual proteins in the protein set (e.g., all proteins in the set, a subset of the protein set, etc.). For example, an aggregated feature value set (e.g., aggregated feature value vector) can be determined for the protein set based on feature value sets (e.g., feature value vectors) for one or more proteins in the protein set. The feature values are preferably aggregated using the feature aggregation model, but can alternatively be otherwise aggregated. In a first example, aggregating feature values includes summing the values for each feature across the proteins of the protein set (e.g., optionally weighted by concentration or abundance). In a second example, aggregating feature values includes predicting an aggregated feature vector based on the feature value set for each protein of the protein set and optionally the respective protein concentration or abundance (e.g., wherein the feature value sets can be concatenated, fed to different input heads, etc.). In a third example, aggregating feature values can include predicting the aggregated feature vector based on the protein sequences of the proteins within the protein set (e.g., wherein the protein sequences can be concatenated, fed to different input heads, etc.).

However, feature values can be otherwise determined.

Determining functional property values for the protein set S180 functions to determine behavior of the protein set. S180 can be performed before S160, after S160, during S600, iteratively, and/or at any other suitable time.

The functional property values are preferably measured and/or otherwise directly determined values for a set of functional properties, but can alternatively be manually assigned, inferred, predicted, or otherwise determined. In a first variant, functional property values are measured and/or extracted from measurements (e.g., measurements determined using any assay and/or assay tool). For example, a sample can be manufactured using the protein set, wherein the functional property values for the protein set are measured using one or more assays and/or assay tools. In an illustrative example, the functional property values are determined for a protein and lipid gel (e.g., wherein the gel manufacturing is prescribed by a context associated with the protein set). The functional property values can be determined using one or more experimental environments, treatments, and/or any other variable (e.g., where the set of functional property values determined in an environment are associated with that variable). In a second variant, the functional property values can be retrieved from a database (e.g., a third-party database). In a third variant, the functional property values can be computationally determined. In a first example of the third variant, the functional property values can be determined based on simulations (e.g., computer simulations of protein dynamics). In a second example of the third variant, the functional property values can be predicted using prediction model (e.g., based on the protein set feature values, etc.).

However, functional property values can be otherwise determined.

The method can optionally include selecting a feature subset S200, which functions to select features which most likely influence (e.g., have a measurable effect on, a significant effect on, a disproportionate effect relative to their concentration, etc.) one or more functional properties and/or to reduce feature space dimensions (e.g., to reduce computational load). S200 can be performed after S100, before S400, during and/or after S30, and/or at any other suitable time. The feature subset can be selected using a feature selection model, using a correlation model, randomly, with human input, and/or be otherwise determined.

In a first variant, the feature subset can be features (e.g., target features) that influence functional properties. In a first embodiment, the feature selection model uses lift analysis (e.g., applied to a prediction model trained to output functional property values based on the feature values) to select the subset of features with lift above a threshold. In a second embodiment, features with prediction model weights above a threshold value are selected as the feature subset, wherein the model weights can be determined during and/or after prediction model training. In a third embodiment, a correlation model can be used to determine features positively and/or negatively correlated to one or more functional properties (e.g., absolute value of correlation coefficient above a threshold, a confidence score above a threshold, etc.).

In a second variant, the subset of features can be determined using any dimensionality reduction technique (e.g., principal component analysis, linear discriminant analysis, etc.).

In a third variant, the subset of features can be determined based on a comparison between a target (e.g., a target protein set and/or target product) and a candidate protein set (e.g., a prototype protein set), wherein the subset of features (e.g., used to predict functional properties for a second candidate protein set) can be selected based on the similarities and/or differences between the respective functional property values. In a first example, a difference between functional property values associated with the target and candidate protein set can be determined (e.g., where values for one or more functional properties differ significantly between the target and candidate). The differing functional property values can define a functional property subset (e.g., target functional properties). These target functional properties can then be used to determine a feature subset (e.g., target features), wherein the feature subset can be the feature(s) mostly likely to influence the functional property subset (e.g., based on a correlation model output). In a second example, a difference between feature values associated with the target and candidate protein set can be determined (e.g., where one or more functional property values differ between the two sets). The features associated with the differing feature values can define the feature subset (e.g., target features).

However, the feature subset can be otherwise selected.

The method can optionally include selecting a functional property subset S250, which functions to reduce functional property space dimensions (e.g., to reduce computational load). S250 can be performed after S100, before S400, during and/or after S300, and/or at any other suitable time. The functional property subset can be selected using a feature selection model, using a correlation model, randomly, with human input, and/or be otherwise determined.

In a first variant, the subset of functional properties can be determined using any dimensionality reduction technique (e.g., principal component analysis, linear discriminant analysis, etc.).

In a second variant, the subset of functional properties can be determined based on a comparison between a target (e.g., a target protein set and/or target product) and a first candidate protein set (e.g., a prototype protein set), wherein the subset of functional properties can be selected based on the similarities and/or differences between the functional property values for the target and the first protein set. In an example, a difference between functional property values associated with the target and candidate protein set can be determined (e.g., where values for one or more functional properties differ significantly between the two sets). The differing functional property values can define a functional property subset (e.g., target functional properties).

However, the functional property subset can be otherwise selected.

Training a prediction model S300 functions to improve functional property value predication, candidate protein set determination (using the prediction model), and/or any other part of the method. S300 can be performed after S100 and/or at any other time.

Figure 6:
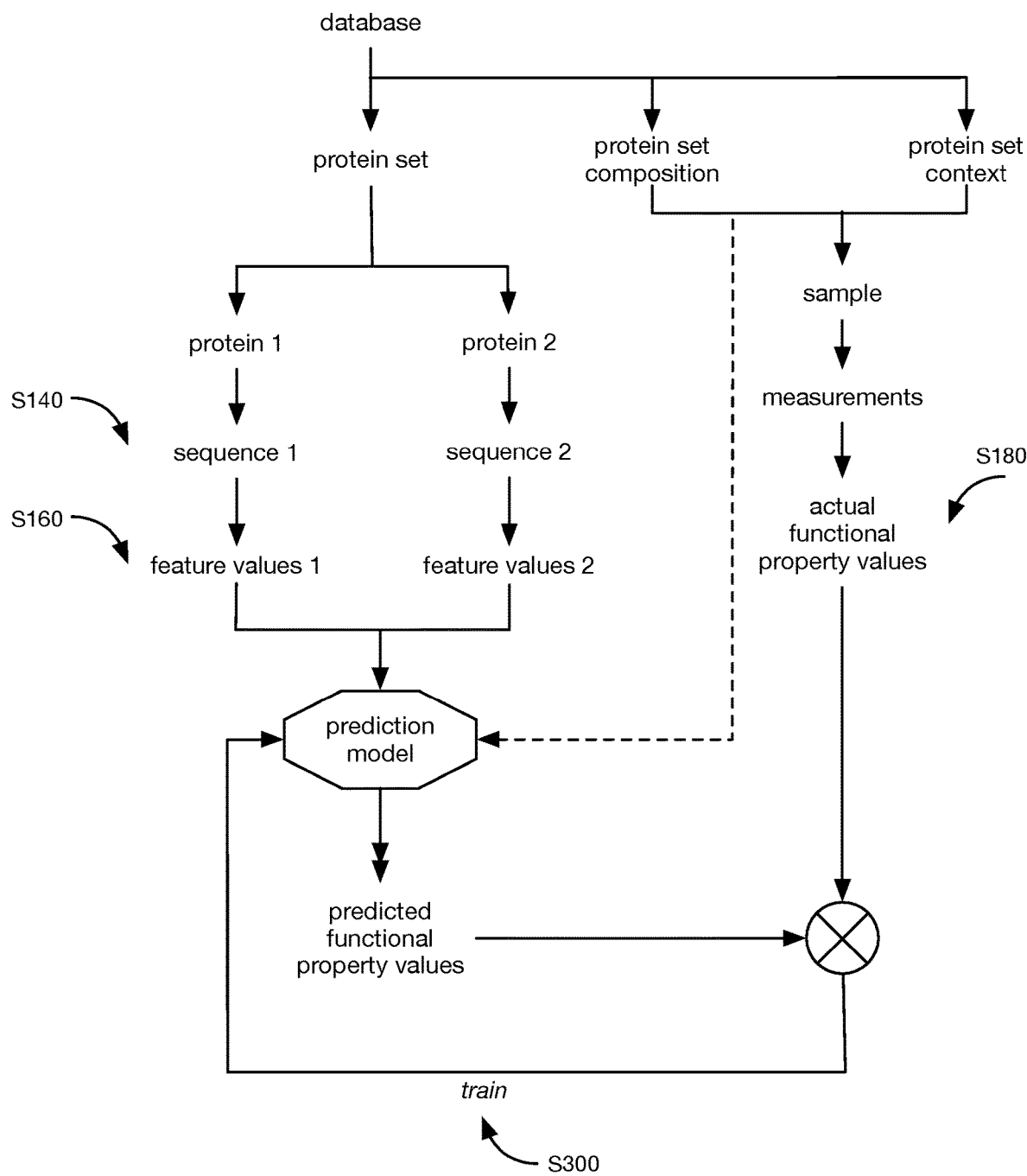
FIG. 6 depicts an embodiment of training a prediction model.
Figure 7A:
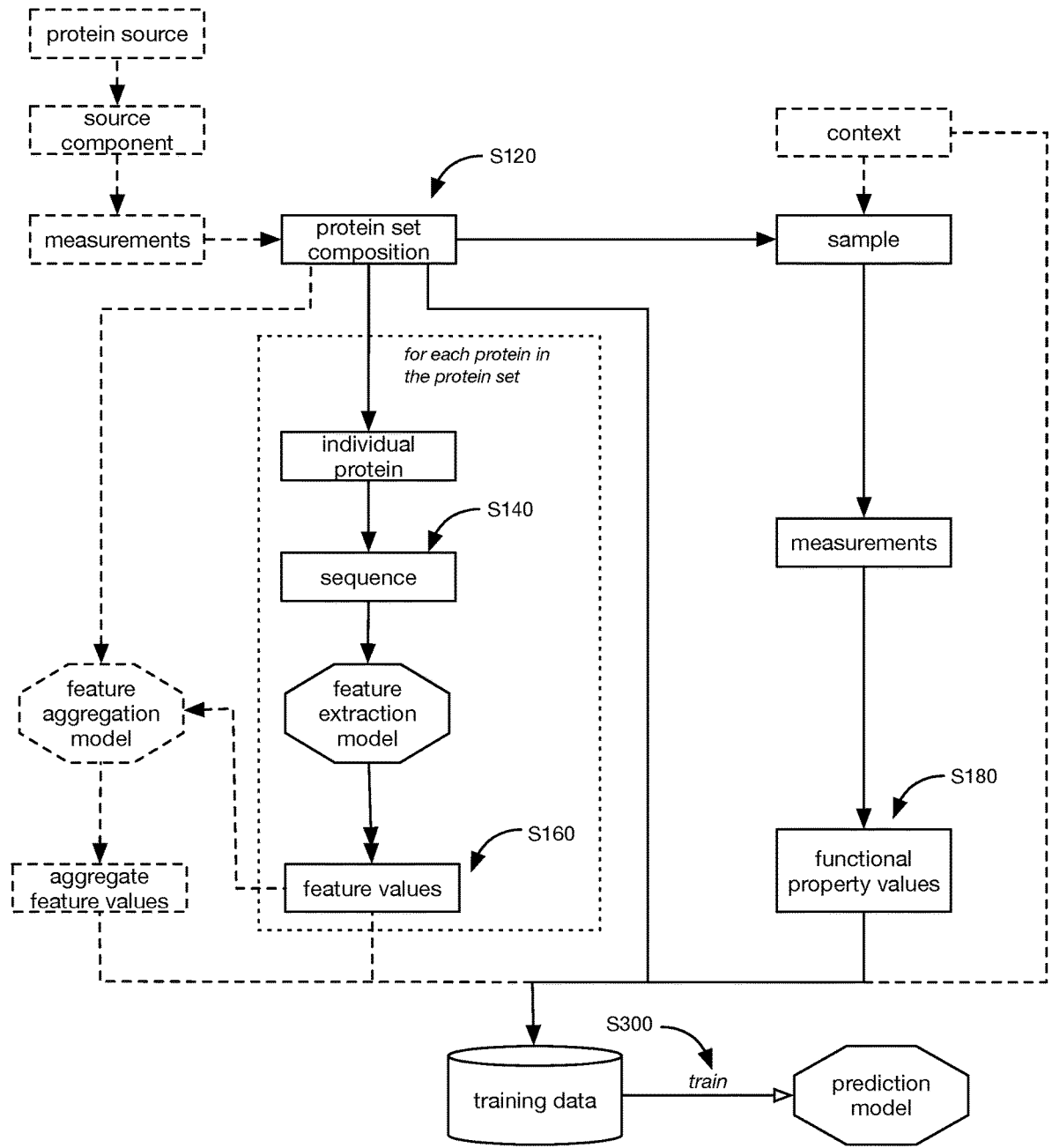
FIG. 7A depicts a first example of training a prediction model to predict functional property values.
Figure 7B:
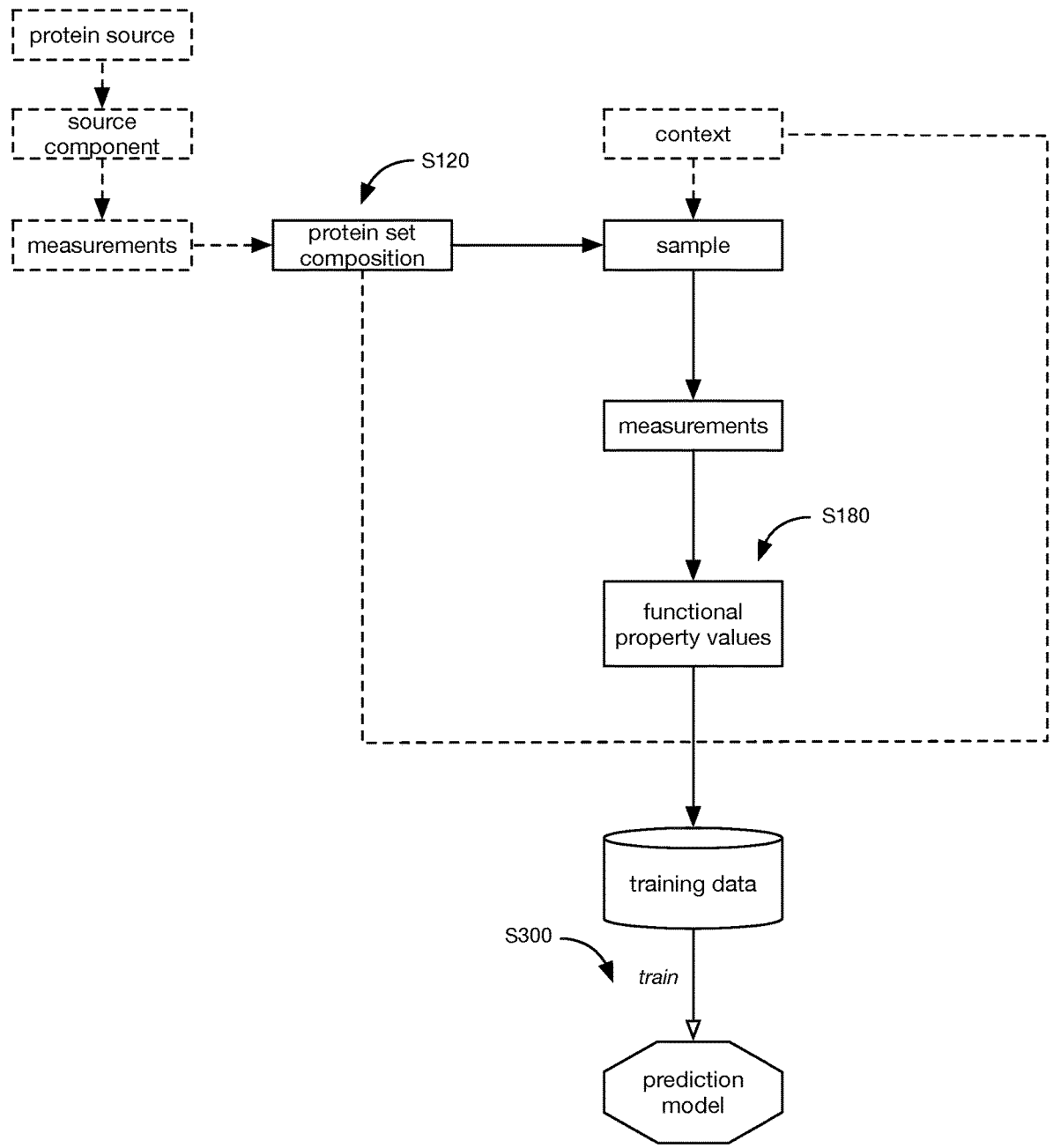
FIG. 7B depicts a second example of training a prediction model to predict functional property values.

In variants, training the prediction model includes determining training data including feature values (e.g., determined via S160) and corresponding functional property values (e.g., determined via S180) for one or more protein sets (e.g., a set of protein sets). The functional property values in the training data are preferably measured, but can alternatively be otherwise determined (e.g., using any other method in S180). The prediction model is then trained using the training data to predict the functional property values for a protein set based on the feature values for the protein set. Examples are shown in FIG. 6, FIG. 7A, and FIG. 7B.

In any variant, the training data can include positive samples (e.g., with no negative samples), wherein the prediction model is trained using positive-unlabeled learning. Alternatively or additionally, the training data can include negative samples, wherein the prediction model can be trained to distance the prediction from the negative samples.

However, one or more prediction models can be otherwise trained.

Determining target characteristic values S400 functions to specify one or more criteria for candidate protein set determination. For example, the candidate protein set can be selected to manufacture an analog for a target product, to replace a target protein set (e.g., a protein set to be replicated and/or replaced, a protein set to be replicated with specified modifications, etc.), to meet a desired set of characteristic values, and/or otherwise used. S400 can be performed after S100 (e.g., after a target protein set has been characterized) and/or at any other time.

The target characteristic values are preferably associated with a characterized protein set (e.g., a characterized target protein set), but alternatively can be associated with an uncharacterized protein set, be associated with a source and/or source component, be associated with a target product (e.g., target food product), be otherwise associated with protein set information, and/or not be associated with a protein set and/or source. The target characteristic values can be all or a subset of: the functional property values, the feature values, the amino acid sequences, and/or any other characteristic value associated with a target: product, source, source component, and/or protein set.

The target characteristic values (e.g., a target characteristic value vector) can be determined manually, automatically, predetermined, with a model (e.g., target features selected using a feature selection model, target functional properties selected using a functional property selection model, etc.), based on a target product and/or target protein set, based on a use case (e.g., the use case for the candidate protein set, for the associated target protein set, etc.), retrieved from a database (e.g., where target functional property values are those associated with a target protein set in the database), measured, and/or be otherwise determined.

In a first variant, the target characteristic values include target feature values. In a first embodiment, the target feature values can be determined for a target protein set using S160 methods. In a specific example, a subset of feature values of the target protein set can be used as the target characteristic values, where the subset can correspond to the feature subset determined in S200. In a second embodiment, target functional property values are used to determine target feature values. In a specific example, a correlation model is used to identify feature values associated with the target functional property values.

In a second variant, the target characteristic values include target functional property values. In a first embodiment, the target functional property values can be determined for a target product and/or protein set using S180 methods. In a second embodiment, the target functional property values can be manually specified (e.g., desired or optimal functional property values for a product, a desired change in functional property values relative to functional property values for a protein set, etc.).

In a third variant, the target characteristic vales can include target feature values and target functional property values (e.g., a combination of the first and second variants).

However, target characteristic values can be otherwise determined.

Determining a candidate protein set based on the target characteristic values S500 functions to determine a protein set that satisfies target criteria (e.g., has desired characteristic values, mimics a target product/protein set, etc.). Additionally or alternatively, S500 functions to determine a candidate protein set for evaluation in S600 (e.g., wherein characterization of the candidate protein set can train the prediction model). S500 can be performed after S400, after S300, during S300 (e.g., as part of training), and/or at any other suitable time.

Determining the candidate protein set can optionally include determining the composition of the candidate protein set (e.g., determining each protein in the set and/or determining the concentration of each protein in the set) and/or selecting a context for the candidate protein set.

In a first variant, determining each protein in the candidate protein set includes individually selecting each individual protein in the candidate protein set from proteins in a candidate group of protein sets. In a second variant, determining each protein in the candidate protein set includes selecting the candidate protein set as a whole from the candidate group of protein sets.

The candidate group of protein sets can include uncharacterized protein sets, partially characterized protein sets (e.g., with feature values but not functional property values), fully characterized protein sets (e.g., with both feature values and functional property values), known or estimated abundant protein sets (e.g., determined based on functional protein labelling), and/or any other set of protein sets. The candidate group can optionally be a subset of the system database (e.g., to reduce the computational resources, to reduce the search space, to constrain all or parts of the selection, etc.). For example, the candidate group can include a subset of protein sources (e.g., candidate protein sources, wherein all or parts of the protein sets associated with each candidate protein source are included), a subset of protein sets, and/or any other subset. In a first specific example, an evolutionary tree is used to identify protein sources evolutionarily related to a target protein source, wherein the candidate group includes protein sets associated with the identified protein sources. In a second specific example, the candidate group includes a set of protein sets with target feature values (e.g., within a threshold similarity to target feature values).

Each protein set in the candidate group can optionally be associated with one or more concentrations and/or contexts. For example, each protein set can be associated with a predetermined set of possible values for each concentration and context parameter (e.g., a protein set can be associated with each unique combination of possible compositions and context values). In an illustrative example, a protein set in the candidate group includes [Protein 1, Protein 2]; the possible compositions for the protein set include: [70%, 30%], [30%, 70%], and [50%, 50%]; the possible contexts for the protein set include: [combine with canola oil, heat to 65° C., glycosylation of Protein 1], [combine with kokum butter, heat to 65° C., glycosylation of Protein 1], [combine with canola oil, heat to 72° C., glycosylation of Protein 1], [combine with kokum butter, heat to 72° C., glycosylation of Protein 1], [combine with canola oil, heat to 65° C., no glycosylation of Protein 1], [combine with kokum butter, heat to 65° C., no glycosylation of Protein 1], [combine with canola oil, heat to 72° C., no glycosylation of Protein 1], and [combine with kokum butter, heat to 72° C., no glycosylation of Protein 1].

The candidate protein set can be determined based on: the target and candidate protein set's characteristic values (e.g., functional property values, feature values, etc.), estimated abundance and/or ease of extraction (e.g., determined based on the protein set's functionality, the protein source, the source component, etc.), the database, and/or any other factor. Any candidate protein set determination method can optionally be supplemented based on protein source and/or source component information (e.g., where the probability of selecting a protein set as the candidate protein set increases if the protein set is likely to be abundant within the protein source and/or the protein source itself is likely to be abundant relative to a threshold).

In a first variant, the candidate protein set is determined using optimization approaches (e.g., Bayesian optimization, machine learning recommender systems, etc.). For example, the candidate protein set can be selected as a training protein set for characterization (e.g., to expand the training data for use in S300), wherein optimization approaches can be used to reduce (e.g., minimize) the number of additional training protein sets that are needed to train the prediction model and/or to identify a candidate protein set that satisfies the target criteria.

Figure 9:
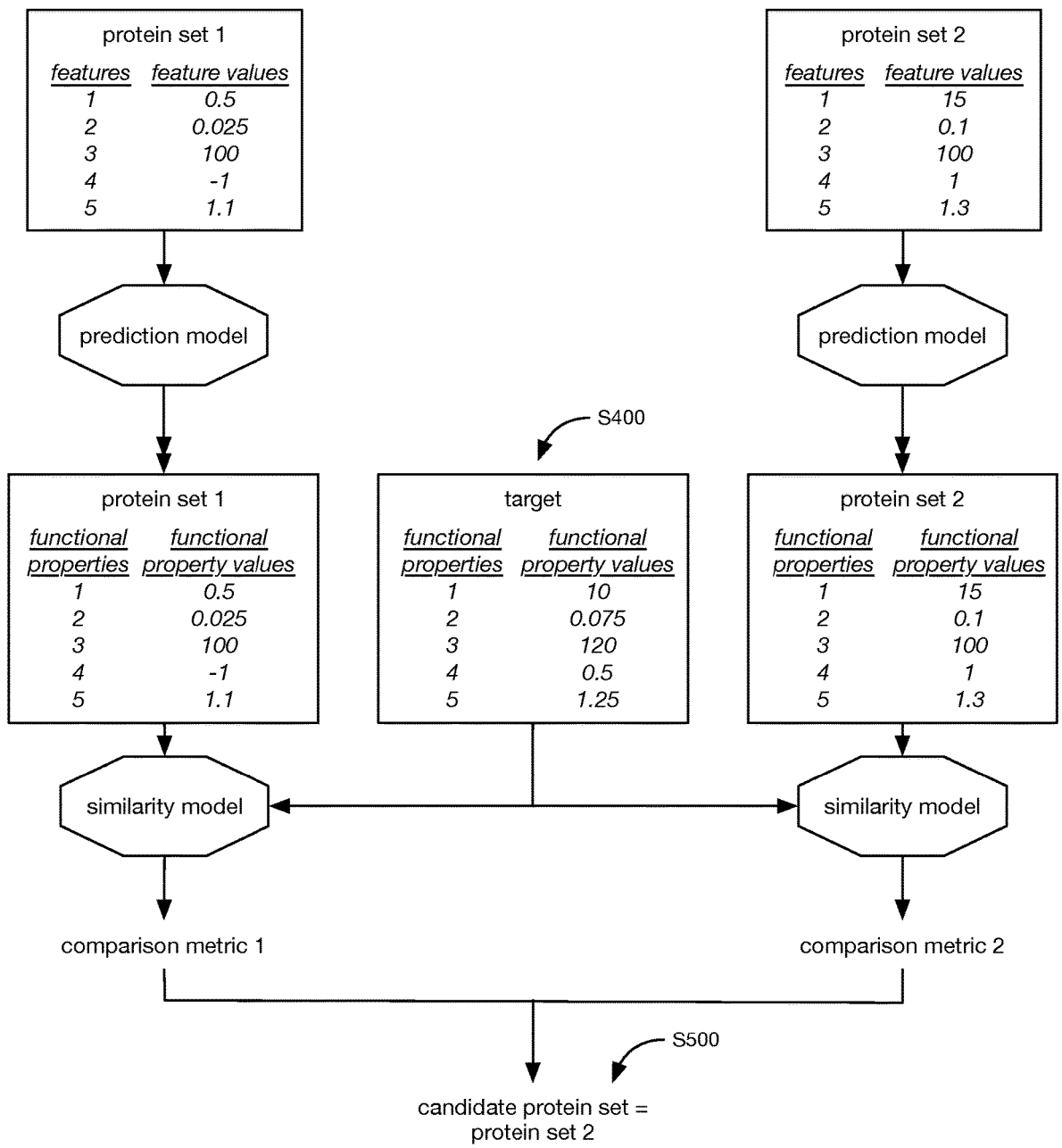
FIG. 9 depicts an illustrative example of determining a candidate protein set.

In a second variant, the candidate protein set can be determined by comparing (e.g., matching) one or more characteristic values using a similarity model to generate a comparison metric (e.g., example shown in FIG. 9). For example, characteristic values for each protein set in the candidate group (e.g., for each unique protein set composition and context pair) can be predicted (e.g., using the prediction model), wherein the predicted characteristic values are compared to the target characteristic values to generate the comparison metric. The candidate protein set (e.g., with associated composition and context) can then be determined based on the comparison metric (e.g., selecting the protein set with the minimum or maximum comparison metric, selecting a protein set with a comparison metric above or below a threshold, selecting the protein set using a protein set determination model, etc.).

In a first embodiment, the candidate protein set's predicted functional property values can be compared to target functional property values (e.g., for an analogous set of functional properties). For example, the candidate protein set's functional property values are predicted using the prediction model (e.g., based on feature values, based on context, etc.).

In a second embodiment, the candidate protein set's feature values can be compared to target feature values. For example, a match between positive target feature values and candidate protein set feature values can increase the probability of selection of the candidate protein set, whereas a match between negative target feature values and to candidate protein set feature values can the probability of selection.

In a third embodiment, a candidate protein source and/or candidate protein set can be selected based on an evolutionary tree. In a first example, the candidate protein source is selected by identifying a protein source based on a close evolutionary relationship with a target protein source and/or protein source containing a matching candidate protein set. In a second example, the candidate protein set can be selected by identifying close evolutionary relationships between proteins in the candidate protein set and proteins in a target protein set. In a third example, additional candidate protein set(s) can be selected after a first selection event of a first candidate protein set by identifying additional protein set(s) based on close evolutionary relationships to the first candidate protein set.

The candidate protein set can optionally be used to manufacture an analog for a target food product (e.g., dairy analog, meat analog, egg analog, any animal product analog, etc.) and/or any other sample (e.g., product). For example, a protein source associated with the candidate protein set can be selected as an ingredient for manufacturing a product. In a specific example, proteins in the candidate protein set can be extracted and/or isolated from one or more sources, wherein a sample is manufactured (e.g., based on a context associated with the candidate protein set) using the proteins to have the determined candidate protein set composition.

However, the candidate protein set can be otherwise determined.

The method can optionally include evaluating the candidate protein set S600, which functions to determine whether the candidate protein set can be used in an analog for a target product, whether the candidate protein set can be used as a replacement for a target protein set, whether the candidate protein set has the desired (e.g., target) characteristic values, to determine feedback for a model (e.g., for training the prediction model, the protein set determination model, and/or any other model), and/or to compare the functional property values of the candidate protein set to one or more other functional property values.

S600 can be performed after S500, after S180 (e.g., after the candidate protein set is characterized with functional property values), iteratively (e.g., until a stop condition is met, such as substantial similarity to the target), and/or at any other time. A search for a protein set can be continued (e.g., iteratively performing S500 and S600) until a candidate protein set satisfies a set of target criteria (e.g., stopping when the evaluation indicates that the candidate protein set characteristic values fall within target ranges), until a comparison metric is below or above a threshold, for a predetermined number of iterations, and/or until any other stop condition is met. In an example, the target criteria include one or more ranges of characteristic values based on target characteristic values (e.g., predetermined ranges around the target characteristic values).

S600 can include: determining functional property values for the candidate protein set (e.g., S180 performed for the candidate protein set), and determining a comparison metric based on the resultant functional property values (e.g., using the similarity model). In an example, determining functional property values for the candidate protein set includes manufacturing a sample containing the candidate protein set (e.g., at a protein composition determined in S500 and/or using a context determined in S500), wherein the sample is subjected to assays to measure functional property values.

The sample (e.g., target food replica) can be manufactured by mixing the protein set with a set of other ingredients (e.g., plant-derived ingredients, such as fats, oils, sugars, etc.) and processing the mixture (e.g., by heating, reacting, inoculating, fermenting, etc.). Alternatively, the sample can be manufactured by gelling the protein, then using the gel as an ingredient. The manufactured samples can be entirely or mostly plant-derived (e.g., more than 70%, 80%, 90%, 99%, etc. plant-derived components by weight or volume).

In a first embodiment, the comparison metric can be based on a comparison between the candidate protein set's measured functional property values and predicted functional property values (e.g., predicted functional property values for the candidate protein set determined using the prediction model). In a second embodiment, the comparison metric can be based on a comparison between the candidate protein set's measured functional property values and target functional property values (e.g., the functional property values of a target protein set). In variants, a comparison metric above or below a threshold (e.g., a significant difference between the actual and target and/or predicted functional property values) corresponds to negative feedback in model training (e.g., S400 and/or any other model training).

However, the candidate protein set can be otherwise evaluated.

The method can optionally include determining interpretability and/or explainability of the trained prediction model, which can be used to select features, select functional properties, identify errors in the data, identify ways of improving the prediction model, increase computational efficiency, determine influential features and/or values thereof, determine influential functional properties and/or values thereof, and/or otherwise used. Interpretability and/or explainability methods can include: local interpretable model-agnostic explanations (LIME), Shapley Additive explanations (SHAP), Ancors, DeepLift, Layer-Wise Relevance Propagation, contrastive explanations method (CEM), counterfactual explanation, Protodash, Permutation importance (PIMP), L2X, partial dependence plots (PDPs), individual conditional expectation (ICE) plots, accumulated local effect (ALE) plots, Local Interpretable Visual Explanations (LIVE), breakDown, ProfWeight, Supersparse Linear Integer Models (SLIM), generalized additive models with pairwise interactions (GA2Ms), Boolean Rule Column Generation, Generalized Linear Rule Models, Teaching Explanations for Decisions (TED), and/or any other suitable method and/or approach.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method, comprising:
  for each protein mixture in a group of protein mixtures:
    for each protein in the protein mixture:
      determining an amino acid sequence; and
      extracting a feature value vector from the amino acid sequence;
    for the protein mixture:
      determining a set of amino acid feature values based on the feature value vectors and relative proportions of proteins within the protein mixture;
      determining a set of context feature values based on manufacturing specifications for manufacturing a sample using the protein mixture; and
      predicting a functional property value for the protein mixture by inputting the set of amino acid feature values and the set of context feature values into a trained prediction model, wherein the trained prediction model is trained using training data comprising, for each training protein mixture in a group of training protein mixtures: a measured functional property value, amino acid sequences, and manufacturing specifications;
  selecting a protein mixture from the group based on comparisons between a target functional property value measured for a dairy protein mixture and the predicted functional property value for each protein mixture; and
  manufacturing a dairy analog food product, wherein each protein in the selected protein mixture is extracted from a plant source, and wherein the extracted proteins are used as ingredients in the dairy analog food product.

2. The method of claim 1, further comprising predicting the relative proportions of proteins within the protein mixture based on a source from which the protein mixture is derived.

3. The method of claim 1, wherein determining the set of amino acid feature values comprises aggregating the feature value vectors based on the relative proportions of the proteins within the protein mixture.

4. The method of claim 3, wherein aggregating the feature value vectors comprises weighting the feature value vectors based on the relative proportions of the proteins within the protein mixture.

5. The method of claim 3, wherein aggregating the feature value vectors comprises using a feature aggregation model, wherein the feature aggregation model is a trained machine learning model.

6. The method of claim 5, wherein the feature aggregation model is trained using multiple instance learning.

7. The method of claim 1, wherein the manufacturing specifications for the protein mixture comprise at least one of temperature, salt level, pH level, macronutrient ingredients, or microbial ingredients.

8. The method of claim 1, wherein the set of context feature values is further determined based on modifications to a protein in the protein mixture.

9. The method of claim 8, wherein the modifications comprise at least one of glycosylation, glycation, phosphorylation, or acylation.

10. The method of claim 1, wherein extracting the feature value vector comprises determining the feature value vector based on k-mers associated with the amino acid sequence.

11. The method of claim 1, wherein the feature value vector comprises values for at least one of: pseudo structure status composition (PseSSC), pseudo amino acid composition (PseAAC), or composition, transition, and distribution (CTD).

12. The method of claim 1, wherein the predicted functional property value comprises a value for at least one of: texture, melt, flavor, chemical properties, denaturation point, particle size, interactions with molecules, or protein aggregation.

13. The method of claim 1, further comprising selecting the group of protein mixtures based on a set of candidate protein sources, wherein each protein mixture in the group of protein mixtures corresponds to a candidate protein source.

14. The method of claim 1, wherein the selected protein mixture is further selected based a second predicted functional property value for each protein mixture.

15. The method of claim 1, wherein manufacturing the dairy analog food product comprises gelling the extracted proteins.

16. The method of claim 1, wherein the measured function property value comprises at least one of a melt measurement or a texture measurement.

17. The method of claim 1, wherein the training data comprises, for each training protein mixture in the group of training protein mixtures:
  training amino acid feature values determined based on the amino acid sequences for the training protein mixture; and
  training context feature values determined based on the manufacturing specifications for the training protein mixture;
wherein the training amino acid feature values and the training context feature values are labeled with the measured functional property value.

18. The method of claim 1, wherein each protein mixture comprises a subset of proteins in a source, wherein the subset of proteins is selected based on a concentration of each protein in the source.

* * * * *